US006841617B2

(12) United States Patent
Jeong et al.

(10) Patent No.: US 6,841,617 B2
(45) Date of Patent: Jan. 11, 2005

(54) THERMOGELLING BIODEGRADABLE AQUEOUS POLYMER SOLUTION

(75) Inventors: Byeong Moon Jeong, Richland, WA (US); Anna Gutowska, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 291 days.

(21) Appl. No.: 09/833,460

(22) Filed: Apr. 11, 2001

(65) Prior Publication Data

US 2002/0173586 A1 Nov. 21, 2002

Related U.S. Application Data

(60) Provisional application No. 60/236,926, filed on Sep. 28, 2000.

(51) Int. Cl.$^7$ .................... C08L 67/04; C08L 71/02; C08G 63/08; A61K 31/765
(52) U.S. Cl. .................... 524/845; 524/504; 524/505; 524/601; 528/354; 424/78.17; 424/486
(58) Field of Search .................... 524/845, 504, 524/505, 601; 528/354; 424/78.17, 486

(56) References Cited

U.S. PATENT DOCUMENTS

| | | | |
|---|---|---|---|
| 4,438,253 A | 3/1984 | Casey et al. .................... 528/86 |
| 4,526,938 A | 7/1985 | Churchill et al. |
| 4,946,686 A | 8/1990 | McClelland et al. ........ 424/473 |
| 5,213,580 A | 5/1993 | Slepian et al. |
| 5,278,201 A | 1/1994 | Dunn et al. .................... 523/113 |
| 5,449,513 A | 9/1995 | Yokoyama et al. |
| 5,462,990 A | 10/1995 | Hubbell et al. ............ 525/54.1 |
| 5,575,815 A | 11/1996 | Slepian et al. |
| 5,634,946 A | 6/1997 | Slepian |
| 5,646,131 A | 7/1997 | Badwan et al. ................ 514/58 |
| 5,662,609 A | 9/1997 | Slepian |
| 5,674,287 A | 10/1997 | Slepian et al. |
| 5,702,717 A | 12/1997 | Cha et al. .................... 424/425 |
| 5,749,915 A | 5/1998 | Slepian |
| 5,749,922 A | 5/1998 | Slepian et al. |
| 5,843,156 A | 12/1998 | Slepian et al. |
| 5,858,746 A | 1/1999 | Hubbell et al. ............. 435/177 |
| 6,004,573 A | * 12/1999 | Rathi et al. .................... 424/426 |
| 6,007,845 A | * 12/1999 | Domb et al. ................. 424/501 |
| 6,060,582 A | 5/2000 | Hubbell et al. ............. 528/354 |
| 6,083,524 A | 7/2000 | Sawhney et al. ........... 424/426 |
| 6,117,949 A | 9/2000 | Rathi et al. .................. 525/415 |
| 6,290,729 B1 | 9/2001 | Slepian et al. |
| 6,352,682 B2 | 3/2002 | Leavitt et al. |
| 6,443,941 B1 | 9/2002 | Slepian et al. |
| 2001/0034050 A1 | 10/2001 | Chilkoti |
| 2002/0032309 A1 | 3/2002 | Deming et al. |
| 2002/0168319 A1 | 11/2002 | Filler et al. |
| 2003/0035838 A1 * | 2/2003 | Prokop ....................... 424/469 |

FOREIGN PATENT DOCUMENTS

| | | |
|---|---|---|
| WO | WO 95/00162 | 1/1995 |
| WO | WO 9603112 | 2/1996 |
| WO | WO 98/55147 | 12/1998 |
| WO | WO 99/07343 | 2/1999 |
| WO | WO 99/18142 | 4/1999 |
| WO | WO 00/21574 | 4/2000 |
| WO | WO 00/56774 | 9/2000 |
| WO | WO 01/67104 | 9/2001 |
| WO | WO 02/26215 | 4/2002 |

OTHER PUBLICATIONS

Deming, Timothy J., "Facile synthesis of block copolypeptides of defined architecture," *Nature*, vol. 390, pp. 386–390 (Nov. 1997).

Alexandridis, P. et al., "Micellization of Poly(ethykene oxide)–Poly(propylene oxide)–Poly(ethylene oxide) Triblock Copolymers in Aqueous Solutions. Thermodynamics of Copolymer Association." p. 2414–2425. 1994.

Bellare, Jr. et al., "Controlled Environment Vitrification System: An Improved Sample Preparation Technique." p. 87–111. 1988.

Brown, W. et al., "Macelle and Gel Formation in a Poly(ethylene oxide) Poly(propylene oxide) Poly(ethylene oxide) Triblock Copolymer Water Solution. Dynamic and Static Light Scattering and Oxcillatory Sheer Measurements." p. 1850–1858 1991.

Cau, F. et al., "HNMR Relaxation Studies of the Micellization of a Poly(ethylene oxide)–Poly(propylene oxide)–Poly(ethylene oxide) Triblock Copolymer in Aqueous Solution." p. 170–178. 1996.

Chen, G. et al., "Graft Copolymers That Exhibit Temperature–Induced Phase Transitions Over a Wide Range of pl1." p. 49–52. 1995.

Deng, Y. et al., "Thermodynamics of Micellisation and Gelation of Oxyethylene Oxypropylene Diblock Copolymers in Aqueous Solution Studied by Light Scattering and Differential Scanning Calorimetry" p. 1441–1446 1992.

Hill–West, JL. et al., "Inhibition of Thrombosis and Intimal Thickening by in situ Photopolymerization of Thin Hydrogel Barriers." p. 5967–5971. 1994.

Israelachvili, JN. "Intermolecular and Surface Forces." p. 102–106 & 207–208. 1985.

(List continued on next page.)

Primary Examiner—Tae H. Yoon
(74) Attorney, Agent, or Firm—Klarquist Sparkman, LLP

(57) ABSTRACT

Disclosed is a thermogelling biodegradable aqueous polymer solution useful in providing a bioactive agent delivery system. The present invention provides a thermogelling biodegradable aqueous polymer solution with a polyethylene glycol (PEG) block and a biodegradable polyester block, where the blocks are linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

17 Claims, 13 Drawing Sheets

OTHER PUBLICATIONS

Jeong, B. et al., "Biodegradable Block Copolymers as Injectable Drug–Delivery Systems." p. 860–862. 1997.

Jeong, B. et al., "Biodegradable Thermoreversible Getting Polymer With a Maximum Modulus at Body Temperature." p. 1–13. 2000.

Jeong, B. et al., "Biodegradable Thermosensitive Micelles of PEG–PLGA–PEG Triblock Copolymers." p. 185–193. 1999.

Jeong, B. et al., "Drug Release From Biodegradable Injectable Thermosensitive Hydrogel of PEG–PLGA–PEG Triblock Copolymers." p. 155–163. 2000.

Jeong, B. et al., "In situ Gelation of PEG–PLGA–PEG Triblock Copolymer Aqueous Solutions and Degradation Thereof." p. 171–177. 2000.

Jeong, B. et al., "New Biodegradable Polymers for Injectable Drug Delivery Systems." p. 109–114. 1999.

Jeong, B. et al., "Reverse Thermogelling Biodegradable Polymers PEG–g–PLGA." p. 1–6. No Year.

Jeong, B. et al., "Thermogelling Biodegradable Polymers With Hydrophilic Backbones: PEG–g–PLGA." p. A–F. 2000.

Jeong, B. et al., "Thermoreversible Gelation of PEG–PLGA–PEG Triblock Copolymer Aqueous Solutions." p. 7064–7069. 1999.

Jeong, B. et al., "Thermoreverrsible Gelation of Poly(Ethylene Oxide) Biodegradable Polyester Block Copolymers." p. 751–760. 1998.

Jhon, MS. et al., "Water and Hydrogels." p. 509–522. 1973.

Johnston, TP. et al., "Sustained Delivery of Interleukin–2 From a Polymer 407 Gel Matrix Following Intraperitoneal Injection in Mice." p. 425–434. 1992.

Malmsten, M. et al., "Self–Assembly in Aqueous Block Copolymer Solutions." p. 5440–5445. 1992.

Odian, G. "Principles of Polymerization." p. 512–515. 1981.

Rosiak, JM. et al., "Hydrogels for Biomedical Purposes." p. 335–339. 1995.

Stile, RA. et al., "Synthesis and Characterization of Injectable Poly(N–isopropylacrylamide) –Based Hydrogels That Support Tissue Formation in Vitro." p. 7370–7379. 1999.

Tanodekaew, S. et al., "Gelation of Aqueous Solutions of Diblock Copolymers of Ethylene Oxide and $_{D,L}$–Lactide." p. 3385–3395. 1997.

Thomas, JL. et al., "Tuning The Response of a pH–Sensitive Membrane Switch." p. 2949–2950. 1995.

Wanka, G. et al., "The Aggregation Behavior of Poly–(oxyethylene)–Poly–(oxypropylene)–Poly-
–(oxyethylene)–Block–Copolymers in Aqueous Solution." p. 101–117. 1990.

Wout, ZGM. et al., "Poloxamer $40^7$–Mediated Changes in Plasma Cholesterol and Triglycerides Following Intraperitoneal Injection to Rats." p. 192–200. 1992.

Yang, Z. et al., "Effects of Block Structure on the Micellization and Gelation of Aqueous Solutions of Copolymers of Ethylene Oxide and Butylene Oxide." p. 2371–2379. 1994.

Yu. GE. et al., "Miceiisation and Gelation of Triblock Copoly(oxyethylene/oxypropylene/oxyethylene), F127" p. 2537–2544. 1992.

Zhou, Z. et al., "Light–Scattering Study on the Association Behavior of Triblock Polymers of Ethylene Oxide and Propylene Oxide in Aqueous Solution." p. 171–180. 1988.

Won, YY. et al. "Giant Wormlike Rubber Micelles." p. 960–963. 1999.

Behravesh, E. et al., "Synthesis and Characterization of Triblock Copolymers of Methoxy Poly(ethylene glycol) and Poly (propylene fumarate)." p. A–F. 2001.

Betre, H. et al., "Injectable Elastin–Like Polypeptide for Cartilage Repair," $47^{th}$ Annual Meeting, Orthopaedic Research Society, p. 601 (Feb. 25–28, 2001).

Meyer, DE. et al., "Drug Targeting Using Thermally Responsive Polymers and Local Hyperthermia," *Journal of Controlled Release*, vol. 71, pp. 213–224 (2001).

Moiseev, L., "Temperature–Dependent Properties of Elastin–like Polypeptides (ELP)," http: www.bu.edu mebb calendar of events abstracts moiseev abstract.htm. (Jan. 21, 2000).

Nath, N. et al., "Interfacial Phase Transition of an Environmentally Responsive Elastin Biopolymer Adsorbed on Functionalized Gold Nanoparticles Studies by Colloidal Surface Plasmon Resonance," *J. Am. Chem. Soc.*, vol. 123, pp. 8197–8202 (2001).

Raucher, D. et al., "Enhanced Uptake of a Thermally Responsive Polypeptide by Tumor Cells in Response to its Hyperthermia–mediated Phase Transition," *Cancer Research*, vol. 61, pp. 7163–7170 (Oct. 1, 2001).

"Genetically Engineered Biomolecules May Help Cancer Treatment Delivery," http://www.dukenews.duke.edu/Daily00–01/chil.htm, (Mar. 9, 2001).

Chilkoti, A. et al., "A genetically Engineered Polypeptide Carrier for Thermal Targeting of Therapeutics."

R.T. Piervincenzi Article—Research Interests: Exploring Protein Engineering to Develop Novel Molecular Tools for Improving Applications in the Fields of Drug Delivery and Biosensor Development.

\* cited by examiner

THERMOGELLING BIODEGRADABLE AQUEOUS POLYMER SOLUTION

CROSS REFERENCE TO RELATED APPLICATION

This application claims the benefit under 35 U.S.C. §119(e) of provisional Patent Application Ser. No. 60/236,926 filed Sep. 28, 2000.

FIELD OF THE INVENTION

The disclosure relates to a thermogelling biodegradable aqueous polymer solution composition and methods of use of such polymers for providing in situ forming, biodegradable implants.

BACKGROUND OF THE INVENTION

Materials that gel in situ have recently gained attention as promising implantable drug delivery systems as well as injectable matrices for tissue engineering. There is an emerging need for materials that are biocompatible, promote cellular proliferation and biosynthesis, support physiological loads, and are easily manipulated and synthesized. Materials that gel in situ are promising as they are easily handled and permit cell seeding, they offer the ability to form any desired implant shape, and may be engineered to be biodegradable and biocompatible.

In situ gelation is the bases of injectable systems that eliminate the need for surgical procedures and offers the advantage of the ability to form any desired implant shape. The change in molecular association can be driven by changes in temperature, pH, or solvent composition. Among the candidates of stimuli sensitive systems, organic solvent-free injectable systems are designed by using the thermosensitive sol-to-gel transition of aqueous solution. Such a system enables bioactive agents to be easily entrapped.

To perform as an ideal injectable system, the aqueous solution of a polymer should exhibit low viscosity at formulation conditions and gel quickly at physiological conditions. Considering the biomedical applications, the biocompatibility of the polymers is also an important issue. Therefore, the material should be biodegradable, and by keeping water-rich hydrogel properties it should not induce tissue irritation during the degradation.

In situ gelling of aqueous Poloxamer 407 and N-isopropylacrylamide copolymers have been studied as candidate materials for injectable drug delivery systems and also tissue engineering applications. These materials are, however, non-biodegradable and animal studies demonstrated an increase in triglyceride and cholesterol after intraperitoneal injection of the aqueous Poloxamer 407 solution.[9]

Recently, Jeong et al. reported biodegradable, in situ gelling poly(ethylene glycol-b-(DL-lactic acid-co-glycolic acid)-b-ethylene glycol), (PEG-PLGA-PEG), triblock copolymers. (See U.S. Pat. No. 6,117,949) They exhibited promising properties as an injectable drug delivery system. In vivo studies in rats demonstrated that the copolymer gels were still present after one month. During the degradation, the initially transparent gel became opaque due to preferential mass-loss of hydrophilic PEG rich segments. This change in morphology and the generation of an interface or phase might denature the protein drugs or cause cell deterioration in tissue engineering. In vitro release of porcine growth hormone (PGH) and insulin from the in-situ formed gel stopped after releasing 40–50% of loaded proteins.

Recently, several protein/peptide drugs demonstrated excellent efficacy in clinical trials and have been introduced to the market. With the advent of genetic engineering, proteins/peptides will soon become much more common drugs. However, due to the short plasma half-life and instability of proteins, there are urgent needs for suitable delivery vehicles. Certain drug formulations need a one to two-week delivery system. Moreover, a one to two-day delivery system may be required. For example, ifosfamide, a drug used for germ cell testicular cancer, is administered intravenously for 5 consecutive days. This treatment is repeated every three weeks or after recovery from hematological toxicity. In order to prepare such a short-term delivery system, poly(ethylene glycol) grafted with poly(lactic acid-co-glycolic acid) (PEG-g-PLGA), where hydrophilic PEG is a backbone, is designed. This material is expected to show a different gelation and degradation behavior, and consequently, a different drug release profile as compared to PEG-PLGA-PEG.

The following references disclose processes or compounds useful in this art:

U.S. Pat. No. 5,702,717
U.S. Pat. No. 5,117,949
Hill-West, J. L.; Chowdhury, S. M.; Slepian, M. J.; Hubbell, J. A. *Proc. Natl. Acad. Sci. USA*, 1994, 91, 5967–5971.
Stile, R. A.; Burghardt, W. R.; Healy, K. E. *Macromolecules*, 1999, 32, 7370–7379.
Chen, G. H.; Hoffman, A. S.; *Nature*, 1995, 373, 49–52.
Thomas, J. L.; You, H.; Tirrell, D. J. *Am. Chem. Soc.*, 1995, 117, 2949–2950.
Malstom, M.; Lindman, B. *Macromolecules*, 1992, 25, 5446–5450.
Yang, J.; Pickard, S.; Deng, N. J.; Barlow, R. J.; Attwood, D.; Booth, C. *Macromolecules*, 1994, 27, 670–680.
Jeong, B.; Bae, Y. H.; Lee, D. S.; Kim, S. W. *Nature*, 1997, 388, 860–862.
Johnston, T. P.; Punjabi, M. A.; Froelich, C. J. *Pharm. Res.*, 1992, 9(3), 425–434.
Wout, Z. G. M.; Pec, E. A.; Maggiore, J. A.; Williams, R. H.; Palicharla, P.; Johnston, T. P. *J. Parenteral Sci. & Tech.*, 1992, 46(6), 192–200.
Jeong, B.; Bae, Y. H.; Kim, S. W. *J. Controlled Releases*, 2000, 63, 155–163.
Jeong, B.; Bae, Y. H.; Kim, S. W. *J. Biomed. Mater. Res*, 2000, 50 (2), 171–177.
Jeong, B.; Gutowska, A. J. Am. Chem. Soc., 2000, Submitted. Jeong, B. Unpublished Data. 2000.
IFEX Prescription, http://wwvv.ifex.com/ifpre.html, A Bristol-Meyers Squibb Co., Princeton, N.J. 08543
Bellare, J. R.; Davis, H. T.; Scriven, L. E.; Talmon, Y. *J. Electron Microsc. Tech.* 1988, 10, 87–111.
Wanka, G.; Hoffmann, H.; Ulbricht, W. *Colloid Polym. Sci.*, 1990, 268, 101–117.
Tanodekaew, S.; Godward, J.; Heatley, F.; Booth, C. *Macromol. Chem. Phys.*, 1997, 198, 3385–3395.
Odian, G. In *Principles of Polymerization*, $2^{nd}$ ed.; John Wiley & Sons, Inc. Korean Student Ed.: Korea, 1981; p513.
Alexandrisdis, P.; Holzwarth, J. F.; Hatton, T. A. Macromolecules, 1994, 27, 2414–2425.
Discher, B. M.; Won, Y.-Y.; Ege, D. S.; Lee, J. C. M.; Bates, F. S.; Discher, D. E.; Hammer, D. A. *Science*, 1999, 284, 1143–1146.
Won, Y.-Y.; Davis, H. T.; Bates, F. S. *Science*, 1999, 283, 960–963.
Brown, W.; Schillen, K.; Almgren, M.; Hvidt, S.; Bahadur, P. *J. Phys. Chem.*, 1991, 95, 1850–1858.

Cau F.; Lacelle, S. *Macromolecules*, 1996, 29, 170–178.

Jeong, B.; Bae, Y. H.; Kim, S. W. *Colloids and Surfaces B: Biointerfaces*, 1999, 16: 185–193.

Zhou, Z.; Chu, B. *J. colloid and Interface Science*, 1988, 126(1): 171–180.

Deng, Y.; Yu, G. E.; Price, C.; Booth, C. *J. Chem. Soc. Faraday Trans.* 1992, 88(10), 1441–1446.

Yu, G. E.; Deng, Y.; Dalton, S.; Wang, Q. G.; Attwood, D.; Price, C.; Booth, C. *J. Chem. Soc., Faraday Trans.* 1992, 88 (17), 2537–2544.

Jeong, B.; Bae, Y. H.; Kim, S. W. *Macromolecules* 1999, 32, 7064–7069.

Israelachivili, J. N. *Intermolecular and Surface Forces*, Academic Press, New York, 1985.

Feil, H.; Bae, Y. H.; Feijen, J.; Kim, S. W. *Macromolecules*, 1993, 26, 2496–2500.

Jeong, B.; Lee, D. S.; Shon, J. I.; Bae, Y. H.; Kim, S. W. *J. Polym. Sci. Polym. Chem.* 1999, 37, 751–760.

SUMMARY OF THE INVENTION

The present invention provides a thermogelling biodegradable aqueous polymer solution with a polyethylene glycol (PEG) block and a biodegradable polyester block, where the blocks are linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

It is an object of the present invention to provide a thermogelling biodegradable polymer solution having utility as a bioactive agent delivery system.

A further object of this invention is to provide a drug delivery system that can be injected parenterally.

Another object of this invention is to provide a drug delivery system that allows control of polymer degradation rate or duration of a sustained gel by controlling the number of branches linked to the backbone of the structure or by mixing a first polymer comprising the formula $A_n(B)$ with at least one other polymer comprising the formula $A_n(B)$, wherein the first polymer is different from said at least one other polymer.

Still another object of this invention is to provide a drug delivery system that allows control of the stability of drugs and drug dosage from one day to two months.

Another object of this invention is to provide block copolymer drug delivery systems that are biodegradable.

Still another object of this invention is to provide block copolymer drug delivery systems that demonstrate desirable release rates.

Another object of this invention is to provide injectable block copolymer drug delivery systems that are in solution at room temperature or lower and gel at or about physiological temperature.

Yet another object of this invention is to provide injectable drug delivery systems that eliminate the need for surgical procedures and offers the advantage of the ability to form any desired implant shape.

Still another object of this invention is to provide stimuli sensitive, organic solvent-free injectable drug delivery systems that are designed by using the thermosensitive sol-to-gel transition of aqueous solutions.

Yet another object of this invention is to provide an aqueous solution of a polymer that exhibits low viscosity at formulation conditions and gels quickly at physiological conditions.

Still yet another object of this invention is to provide drug delivery systems that can provide desired release rates by varying the ratio of polyethylene glycol (PEG) block and a biodegradable polyester block.

Additional objects and advantages of this invention will become apparent from the following summary and detailed description of the various embodiments making up this invention.

There is an emerging need for materials that are biocompatible, promote cellular proliferation and biosynthesis, support physiological loads, and are easily manipulated and synthesized. Materials that gel in situ are promising as they are easily handled, permit cell seeding, and they offer the ability to form any desired implant shape. The present invention is well suited for delivery of cells, whereby the thermogelling biodegradable aqueous polymer solution provides a scaffold for tissue repair and organ regeneration. The present invention offers several advantages including: the flowability of the thermogelling biodegradable aqueous polymer solutions can fill any shape of a defect, promotion of tissue integration, easily incorporates live cells and various therapeutic agents (e.g. growth factors), and finally enables minimally invasive placement.

Therefore, another object of this invention is to provide a thermogelling biodegradable polymer solution having utility in tissue engineering.

Still another object of this invention is to provide a thermogelling biodegradable polymer solution having utility as a cell delivery system.

Yet still another object of this invention is to prepare biodegradable solubilizes for hydrophobic drugs. Due to surfactant nature of the PEG-g-PLGA and PLGA-g-PEG, this polymer can be used as a solubilizer for hydrophobic drug formulations.

For a clear and concise understanding of the specification and claims, including the scope given to such terms, the following definitions are provided:

Bioactive Agent: As used herein, a "bioactive agent" shall mean any drug, molecule, biomolecule, or cell.

Drug: As used herein, a "drug" shall mean any organic compound or substance having bioactivity and adapted or used for a therapeutic purpose.

Polypeptide: As used herein, a "polypeptide" shall mean any peptide, polypeptide, oligopeptide, and/or protein used as a drug and shall not be limited by molecular weight, sequence, length, activity or use.

Parenteral: Administering into the body or administered in a manner other than through the digestive tract, as by intravenous or intramuscular injection.

BRIEF DESCRIPTION OF THE DRAWINGS

A more complete appreciation of the invention will be readily obtained by reference to the following description and the accompanying drawings in which like numerals in different figures represent the same structures or elements, wherein.

DETAILED DESCRIPTION

Figure 1:
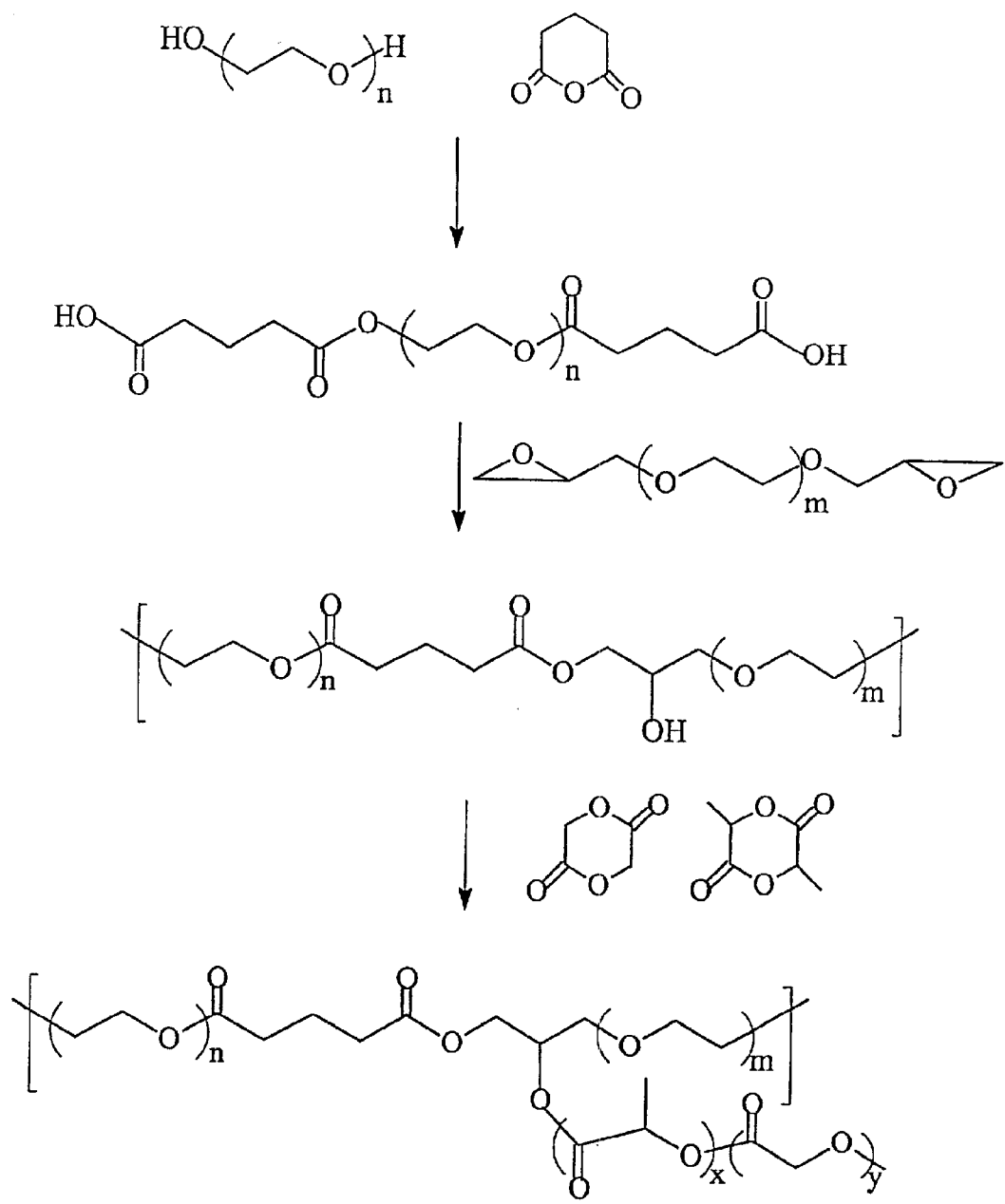
FIG. 1 is a schematic representation of the synthesis of PEG-g-PLGA.

The present invention is a biodegradable polymer solution, comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

The present invention further provides a thermogelling biodegradable aqueous polymer solution which comprises a biodegradable polymer solution, comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B, and an aqueous solution.

The thermogelling biodegradable aqueous polymer solution is preferred when prepared with the formula $A_n(B)$ as described previously and n is between 3 and 10.

The biodegradable polyester block is preferably a member selected from the group consisting of poly(DL-lactic acid), poly(L-lactic acid), poly(glycolic acid), poly(ε-caprolactone), poly(γ-butyrolactone), poly(α-valerolactone), poly(β-hydroxybutyric acid), and their copolymers or terpolymers. It is also preferred that the copolymers and/or terpolymers are selected from the group consisting of poly(DL-lactic acid-co-glycolic acid), poly(L-lactic acid-co-glycolic acid), poly(ε-caprolactone-co-DL-lactic acid), copoly(ε-caprolactone-co-DL-lactic acid-glycolic acid). The above listing of suggested biodegradable polyester blocks is not intended to be all-inclusive. The biodegradable polyester blocks can have a maximum molecular weight of 100,000 with a preferred range of about 1,000 and 30,000, and most preferably between about 1,000 and 10,000. The biodegradable polyester blocks are limited as a result of the desire to accommodate a solubility limit and not because of degradability It is preferred that the polyethylene glycol (PEG) block have an average molecular weight of between about 300 and 20,000 and is more preferably between about 500 and 10,000. The PEG block with a higher molecular weight than 10,000 is hard to be filtered through glomeruli filtration.

The present invention provides an effective biodegradable bioactive agent delivery liquid, comprising an effective amount of bioactive agent contained in thermal gelling biodegradable aqueous polymer solution comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

It is understood that the present invention can make use of any bioactive agent, which can be any drug, molecule, biomolecule, or cell. As well, the present invention can provide as a delivery system for other matter requiring a sustained release rate.

The thermogelling biodegradable aqueous polymer solutions of the present invention are useful as drug delivery systems that provide as a carrier for drugs. A drug is an organic compound or substance having bioactivity and adapted or used for a therapeutic purpose including but not limited to anti-cancer agents, hormones, antibiotics, narcotic antagonists, analgesics, anti-inflammatory agents, anti-depressants, anti-epileptics, anti-malarial agents, immunoactivators, growth factors, gene therapy agents, oligonucleotides, therapeutic peptides and proteins, and combinations thereof. In particular, the present invention provides a very useful delivery system for polypeptide and protein drugs that require a short biodegradation period to accommodate the requirement for a specific sustained release rate due to the short plasma half-life and instability.

Because the polymers of the present invention are composed of hydrophobic and hydrophilic blocks and the surfactant nature, this polymer can be used as a solubilizer for hydrophobic drug formulations. This property enables these polymers to be used as a solubilizer of hydrophobic drugs. Typical cancer drugs, such as Taxol, have good efficacy while they tend to have low solubility in water. The polymers of the present invention can be used as biocompatible solubilizers for such drugs.

The present invention is well suited for delivery of anti-cancer agents. It is preferred that the anti-cancer agents be selected from the group consisting of adriamycin, mitomycin, bleomycin, cisplatin, carboplatin, doxorubicin, daunorubicin, 5-fluouroacil, methotrexate, taxol, taxotere, and actinomycin D. It is understood that other anti-cancer agents may work as well with this invention and the preceding list is not meant to be all-inclusive.

The present invention is equally well suited for delivery of polypeptides. It is preferred that that polypeptides be selected from the group consisting of oxytocin, vasopressin, adrenocorticotropic growth factor (PDGF), prolactin, luliberin or luteinising hormone releasing hormone (LHRH), growth hormone, growth hormone releasing factor, insulin, somatostatin, glucagons, interleukin-2 (IL-2), interferon-α, β,γ (IFN-α,β,γ), gastrin, tetragastrin, pentagastrin, urogastroine, secretin, cacitonin, enkephalins, endorphins, angiotensins, thyrotropin releasing hormone (TRH), tumor necrosis factor (TNF), nerve growth factor (NGF), granulocyte-colony stimulating factor (G_CSF), granulocyte macrophage-colony stimulating factor (M-CSF), rennin, bradykinin, bacitracins, polymixins, colistins, tyrocidin, gramicidines, and synthetic analogues, modifications and pharmacologically active fragments thereof, monoclonal antibodies and soluble vaccines. This list is not all-inclusive and it is understood that other proteins can be used as well.

The present invention is well suited for delivery of cells. The thermogelling biodegradable aqueous polymer solution comprising cells provides a scaffold for tissue repair and organ regeneration as well as for therapeutic use.

A useful aspect of the present invention is method for the delivery of a bioactive agent in a thermogelling polymer matrix to a warm-blooded animal for the controlled release of the bioactive agent. Fundamental to this aspect of the invention is to provide an injectable thermogelling biodegradable aqueous polymer solution which comprises a polyethylene glycol (PEG) block, a biodegradable polyester block, wherein the blocks are linked to form a polymer of a general structure comprising the formula of An(B), where n is greater than 2 and A is selected from the group consisting of a polyethylene glycol block and a biodegradable polyester block, B is selected from the group consisting of a polyethylene glycol block and a biodegradable polyester block, and A is different from B. The thermogelling biodegradable aqueous polymer solution is then mixed with an effective amount of a bioactive agent to form a polymer-bioactive agent mixture, maintained at a temperature below the gelling temperature of the polymer, and provided into a warm blooded animal to form a gel depot as the temperature is raised by the body temperature of the animal to be above the gelling temperature of the polymer. It is recognized that this aspect of the present invention can have various forms of application. For example, it is well suited to use this method of application when it is desired to apply a bioactive agent to a warm-blooded animal during a surgical procedure where a portion of the body of the warm-blooded animal is exposed. By applying the polymer-bioactive agent mixture to an area exposed during surgery will allow the formation of a depot to a specific/desired area.

Another aspect of the present invention is method for the parenteral delivery of a bioactive agent in a thermogelling polymer matrix to a warm-blooded animal for the controlled release of the bioactive agent. Fundamental to this aspect of the invention is to provide an injectable thermogelling biodegradable aqueous polymer solution which comprises a polyethylene glycol (PEG) block, a biodegradable polyester block, wherein the blocks are linked to form a polymer of a general structure comprising the formula of An(B), where n is greater than 2 and A is selected from the group consisting of a polyethylene glycol block and a biodegradable polyester block, B is selected from the group consisting of a polyethylene glycol block and a biodegradable polyester block, and A is different from B. The injectable thermogelling biodegradable aqueous polymer solution is then mixed with an effective amount of a bioactive agent to form a polymer-bioactive agent mixture, maintained at a temperature below the gelling temperature of the polymer, and injected into a warm blooded animal to form a gel depot as the temperature is raised by the body temperature of the animal to be above the gelling temperature of the polymer. This aspect of the invention provides well when it is desired to provide a bioactive agent under controlled release without having to surgically expose a warm-blooded animal. Several injectable routes including intradermal or intracutaneous, subcutaneous or hypodermic, intramuscular, intravenous, and intraspinal can administer the polymer-bioactive agent mixture parenterally.

Having described the invention, the following experimental examples are given. These specific examples are not intended to limit the scope of the invention described in this application.

Experimental Section:

Materials:

DL-lactide (Polyscience) and glycolide (Polyscience) were recrystallized from ethyl acetate. Glutaric anhydride (Aldrich), glutaric acid (Aldrich), stannous octoate (Aldrich), epoxy terminated polyethylene glycol (m.w.:600; Polyscience), poly(ethylene glycol m.w.:1000; Aldrich), and 1,6-diphenyl-1,3,5-hexatriene (DPH; Aldrich) were used as received.

Synthesis: Three-Step Synthesis of PEG-g-PLGA (FIG. 1.)

First, PEGs (m.w.=1000, 38.28 g, 38.28 mmole) were dissolved in 90 ml toluene. Toluene was then distilled off to a final volume of 50 ml to remove water by azeotropic distillation. Carboxylic acid terminated PEG (CPEG) was prepared by reacting PEG with excess amount of glutaric anhydride in the presence of catalytic amounts of glutaric acid. Glutaric anhydride (7.255 g, 80.39 mmole) and glutaric acid (0.042 g, 0.40 mmole) were added and the reaction mixture was stirred at 120° C. for 6 hours. The chemical shifts (ppm) in the spectra are 1.9 (central methylene of glutarate), 2.4 (methylene of glutarate next to carbonyl group), 3.6 (ethylene of PEG), and 4.2 (methylene of PEG connected to glutarate). The one to one area ratio of the peaks at 1.9 ppm and 4.2 ppm indicates the quantitative end group functionalization. Diethyl ether was added to the reaction mixture to precipitate out the carboxylic acid terminated PEG (CPEG). The product was placed under high vacuum (~$10^{-3}$ mm Hg) for 48 hours to remove the residual solvent.

Figure 2:
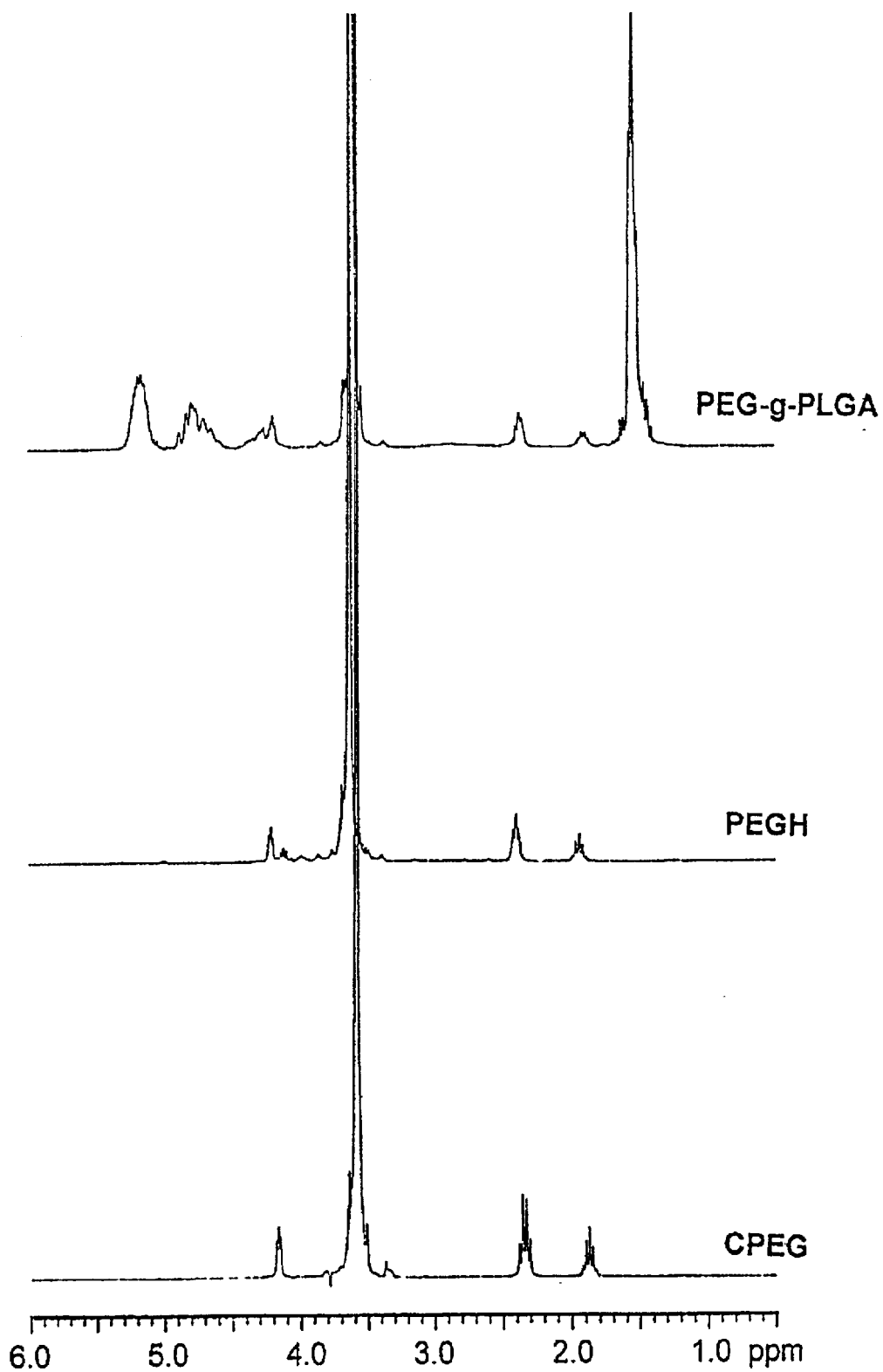
FIG. 2 is a graphical representation of NMR spectra of intermediate and final products of PEG-g-PLGA synthesis.

In the second step, epoxy terminated PEG (EPEG) (m.w.= 600, 5.619 g, 9.36 mmole) was reacted with CPEG (11.50 g, 9.36 mmole) in toluene at 120° C. for 24 hours to prepare PEG with pendant hydroxyl groups (PEGH) along the PEG backbone. The weight average molecular weight ($M_w$) and polydispersity index (PDI) of resulting PEGH, which were determined by GPC, was 3000 and 1.3 relative to polystyrene standards. The peaks at 1.9 ppm and 2.4 ppm come from glutarate. The peaks at 3.6 ppm and 4.3 ppm come from PEG. The small overlapped peaks 3.4 to 4.2 ppm of PEGH come from the connecting methylene or methine moieties between CPEG and EPEG (FIG. 2).

In the third step, DL-lactide (19.2 g, 133.3 mmole) and glycolide (6.4 g, 55.1 mmole) were polymerized in situ on the preformed PEGH backbone at 130° C. for 24 hours, using stannous octoate (76 µL, 0.187 mmole) as a catalyst.

The graft copolymers were precipitated into excess ethyl ether and the residual solvent was removed under vacuum.

Figure 3:
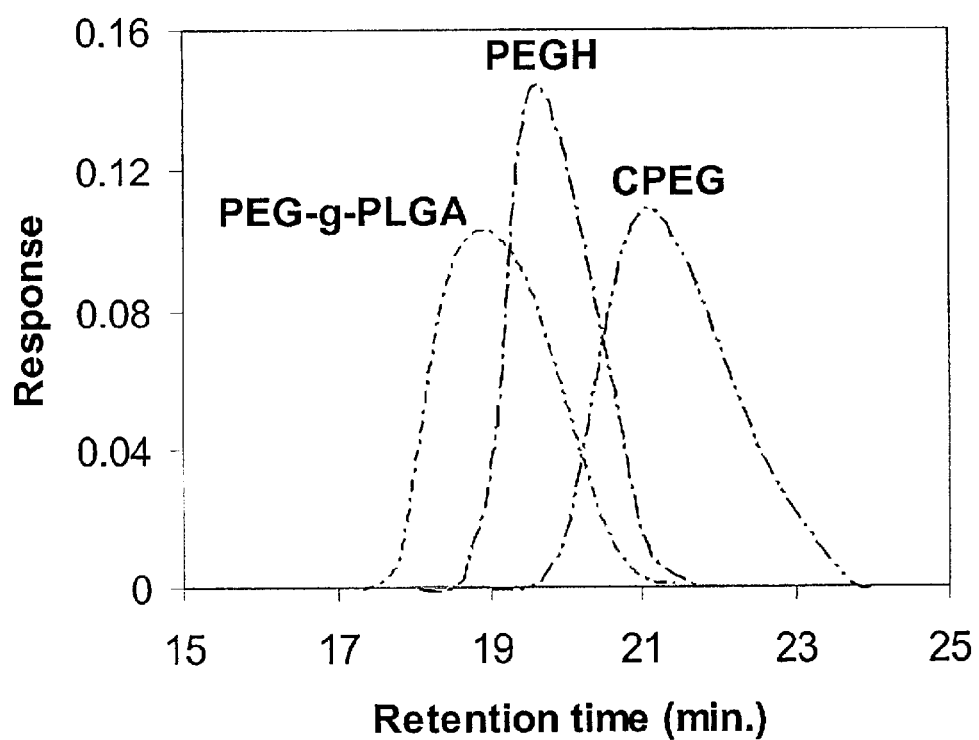
FIG. 3 is graphical representation of a GPC chromatogram of polymers showing progress of reactions.

There are two possibilities of the ring-opening pattern of the epoxy group during the reaction of EPEG and CPEG. The nucleophiles prefer to attack the sterically less hindered side of the epoxy group in the base-catalyzed addition, while ring opening is less regiospecific in cationic polymerization. The GPC chromatogram in FIG. 3 shows the increase in molecular weight by the formation of PEGH from CPEG and EPEG. Assuming a PEGH molecular weight of about 3,000, there are ~2–3 pendant hydroxy groups per each PEGH.

The resultant PEGH was used as an initiator for the ring-opening polymerization of DL-lactide and glycolide in the presence of stannous octoate as a catalyst. H-NMR spectra (FIG. 2) show an ethylene glycol unit at 3.6 ppm, a lactic acid unit at 5.3 ppm (methine) and 1.8 ppm (methyl), and a glycolic acid unit at 4.8 ppm. Composition of the PEG-g-PLGA calculated by $^1$H-NMR was 2.98/2.35/1.00 (ethylene glycol/DL-lactic acid/glycolic acid) in mole ratio. The methylene protons of the epoxy group show up at 2.6 ppm and 2.8 ppm in H-NMR. In the H-NMR spectrum of PEGH and PEG-g-PLGA the epoxy signals are too small to be analyzed quantitatively. Weight average molecular weight ($M_w$) and PDI of PEG-g-PLGA determined by GPC relative to polystyrene standards was 11,000 and 1.3 respectively.

Gel Permeation Chromatography (GPC):

The GPC system (Waters 515) with a refractive Index Detector (Waters 410) and a Light Scattering Detector Mini Dawn (Wyatt Technology) were used to obtain molecular weight and molecular weight distribution. Styragel® HMW 6E and HR 4E columns (Waters) were used in series. Tetrahydrofuran (THF) was used as an eluting solvent.

Cryo-Transmission Electron Microscope (Cryo-TEM):

Using cryo-TEM, a 1% PEG-g-PLGA solution was investigated in the form of vitreous films. Detailed procedures for the sample preparation have been published elsewhere. (Bellare et. al., *Electron Microsc. Tech.* 1999, 10, 87–111.) The liquid films of 10 to 300 nm thickness freely spanning across the micropores in a carbon-coated lacelike polymer substrate were prepared at 23.7° C. with complete control of temperature and humidity, and rapidly vitrified with liquid ethane at its melting temperature (–1800° C.). Imaging was performed using a JEOL 1210 operating at 120 kV. Adequate phase contrast was obtained at a nominal underfocus of ~6 micrometers. Images were recorded on a Gatan 724 multiscan camera, and optical density gradients in the background were digitally corrected.

CMC Determination:

Hydrophobic dye, 1,6-diphenyl-1,3,5-hexatriene (DPH) was dissolved in methanol with a concentration of 0.4 mM. This solution (20 µL) was injected using a microsyringe into 2.0 ml PEG-PLGA polymer aqueous solution with various concentrations between 0.0032 and 0.26 wt. % and equilibrated for 5 hours at 4° C. UV-VIS spectrometer (HP 8453) was used to get the UV-VIS spectra in the range of 280 to 450 nm at 20° C. CMC was determined by the plot of the difference in absorbance at 377 nm and at 391 nm ($A_{377}$–$A_{391}$) versus logarithmic concentration.

Viscosity:

The viscosity of PEG-g-PLGA aqueous solution (22 wt. %) was measured as a function of temperature. A Canon-Fenske viscometer 200 with a viscometer constant of 0.0966 centistokes/sec. was used to measure the viscosity of the polymer solution.

Dynamic Mechanical Analysis:

The sol-gel transition of the graft copolymer aqueous solution (22 wt. %) was investigated using a dynamic mechanical rheometer (Rheometric Scientific: SR 2000). The polymer solution was placed between parallel plates having a diameter of 25 mm and a gap distance of 0.5 mm. The data were collected under controlled stress (4.0 dyne/cm$^2$) and frequency of 1.0 radian/second. The heating and cooling rate was 0.2° C./min.

Sol-Gel Transition:

The sol-gel transition was determined by a test tube inverting method with a temperature increment of 1° C. per step. Polymer aqueous solutions (0.5 g) were prepared in 4 mL vials with inner diameters of 11 mm. The vials were immersed in a water bath at each step for 15 minutes. The sol-gel transition temperature was monitored by inverting the vials, and if there was no flow in 30 seconds, it was regarded as a gel. The transition temperature was determined with ±1° C. accuracy.

NMR Study:

A NMR spectrometer (Varian® VXR 300) was used for $^1$H-NMR and $^{13}$C-NMR to study composition and microenvironment change during sol-to-gel transition. For the $^{13}$C-NMR in $D_2O$, a 22 wt. % PEG-g-PLGA solution was prepared.

Results and Discussion

Micellization:

PEG-g-PLGA is an amphiphilic copolymer and a core-shell structure can be expected in water. The hydrophobic PLGA side chains form a core and the hydrophilic PEG backbones form a shell region. The formation of core-shell structure was investigated by Cryo-transmission electron microscopy (Cryo-TEM) and dye solubilization method.

Figure 4:
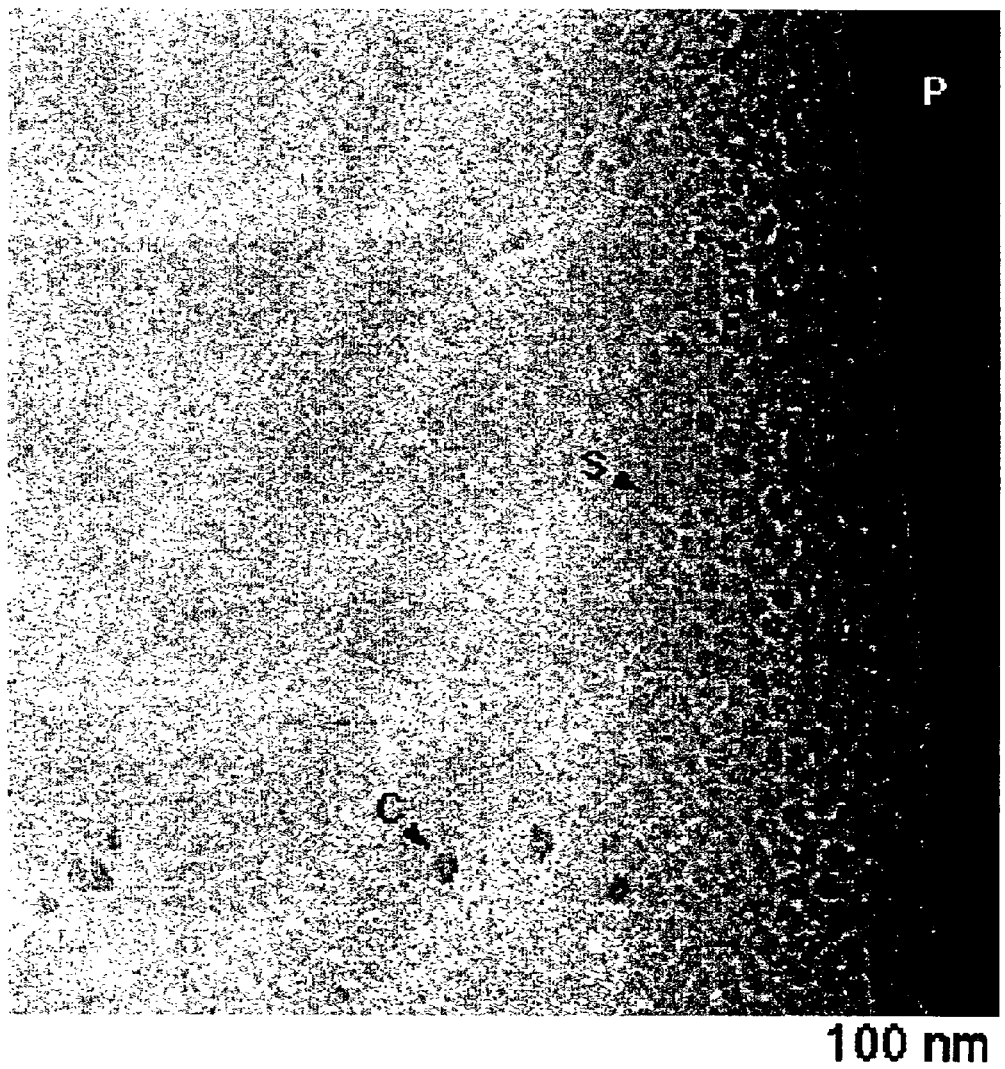
FIG. 4 is a Cryo-TEM image showing micelle formation of the PEG-g-PLGA polymer at a concentration of 1 wt % in water at 23.7° C.

The formation of micelles was directly confirmed by a Cryo-TEM image. An 1 wt. % PEG-g-PLGA solution at 23.7° C. was quenched into a vitrified form at –180° C. The Cryo-TEM image shows closely packed spherical micelles (denoted as S in FIG. 3) on the left side of black stripe. The diameter of a micelle is about 9 nm. (FIG. 4)

Figure 5A:
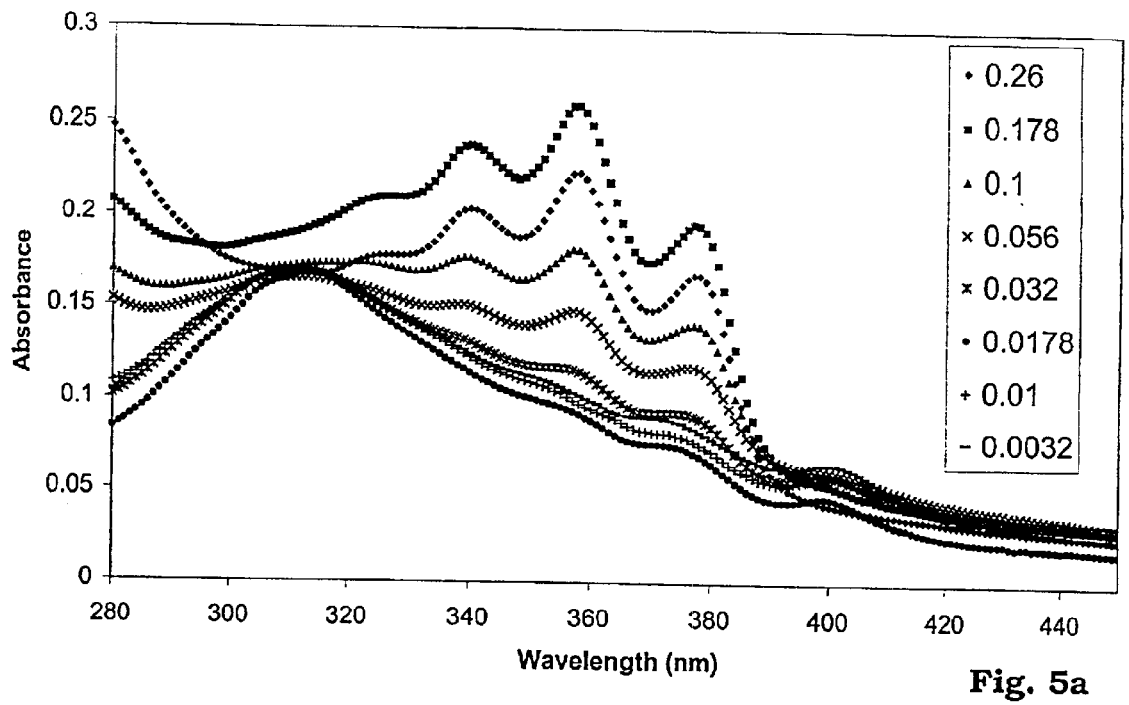
FIG. 5a is a graphical representation of UV spectra showing the formation of core-shell structure of polymers in water at 20° C. where DPH concentration was fixed at 4 μM and polymer concentration varied according to key legend.
Figure 5B:
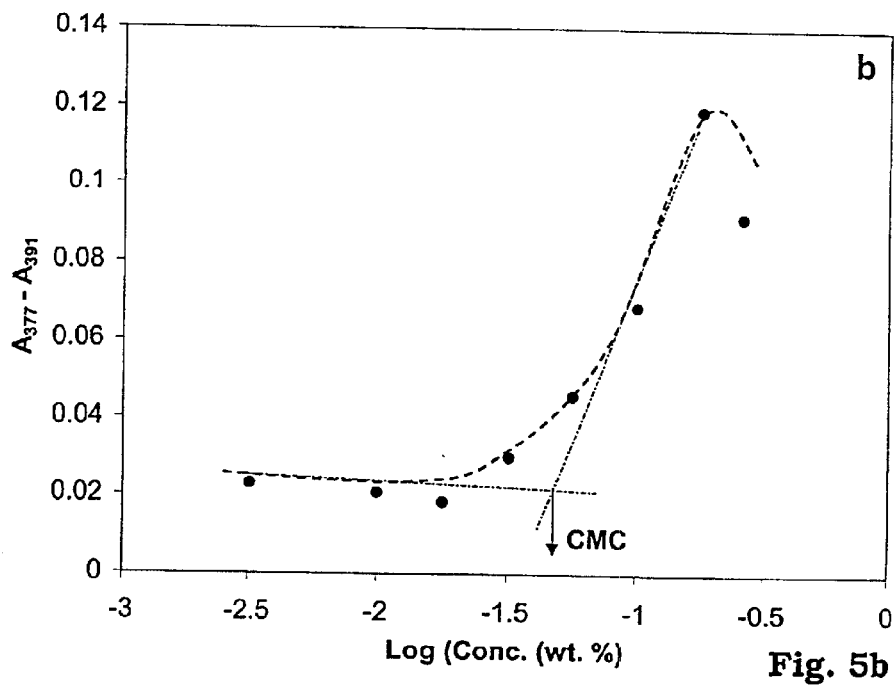
FIG. 5b is a graphical representation of the cmc determination by extrapolation of the difference in absorbance at 377 and 392 nm.

At a fixed concentration of DPH, the polymer concentration was increased from 0.0032 to 0.26 wt. %. The absorption coefficient of the hydrophobic dye (DPH) is much higher in a hydrophobic environment than in water. Thus, with increasing polymer concentration, the absorbance at 377 and 356 nm increased, indicating that the polymers formed a core-shell structure in water creating a hydrophobic environment (FIG. 4-a). The critical micelle concentration (CMC) was determined by extrapolating the absorbance at 377 nm minus absorbance at 391 nm ($A_{377}$–$A_{391}$) versus logarithmic concentration (FIG. 4-b) to compensate for the scattering effect. The CMC value determined by this extrapolation is not precise due to the uncertainty in the line, but it is in a range of 0.01–0.05 wt. % at 20° C. FIG. 5a is a UV spectrum showing the formation of core-shell structure of polymers in water at 20° C. DPH concentration was fixed at 4 µM and polymer concentration varied: 0.0032, 0.01, 0.0178, 0.032, 0.056, 0.010, 0.178, 0.26 wt. %. The increase in absorption band at 377 nm with increasing polymer concentration indicates the formation of a hydrophobic environment, that is, micelles, in water. FIG. 5b shows a CMC determination by extrapolation of the difference in absorbance at 377 nm and at 391 nm.

Figure 6:
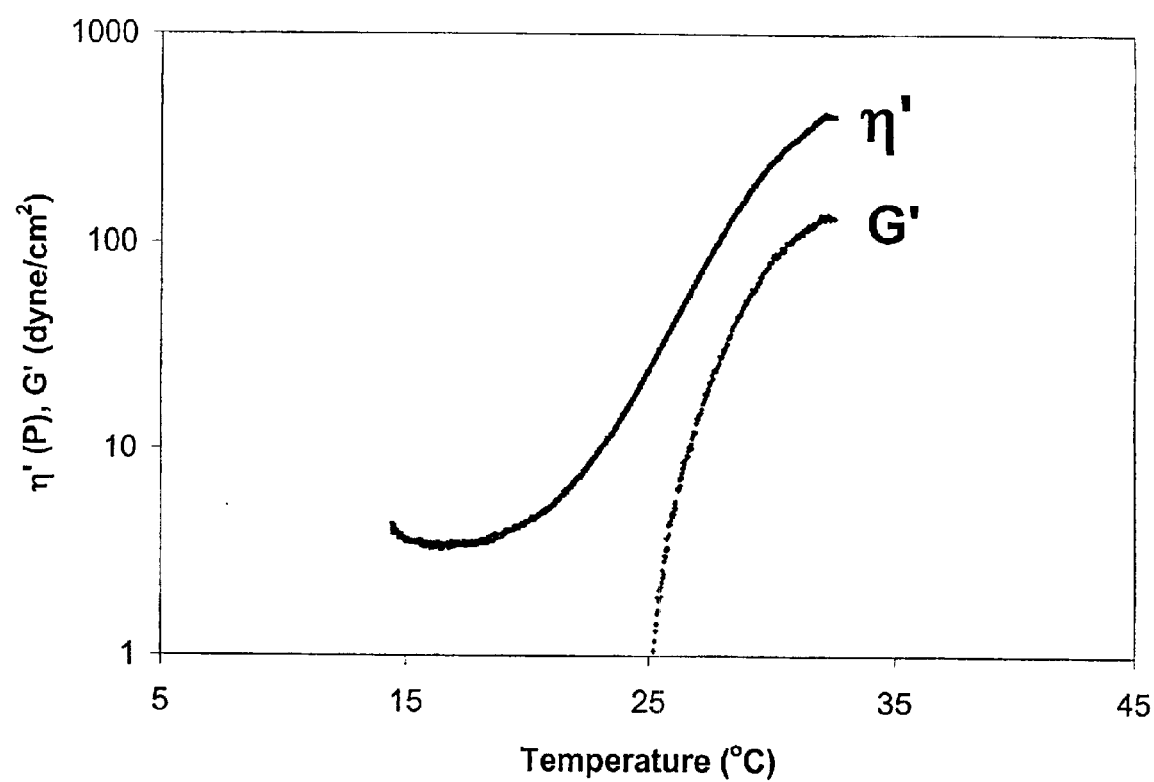
FIG. 6 is a graphical representation of real part (n') of complex viscosity and elastic modulus (G') of 22 wt % PEG-g-PLGA aqueous solutions as a function of temperature.

Sol-Gel Transition:

At high concentrations, the PEG-g-PLGA aqueous solution undergoes a sol-to-gel transition with increasing temperature. The viscosity of a 22 wt. % PEG-g-PLGA aqueous solution that was measured by Cannon-Fenske viscometer was 27 centipoises at 20° C. This viscosity is low enough for an easy formulation of the polymer with pharmaceutical agents that could be injected using a 22-gauge needle. Above the gelation temperature, the viscosity is too high to flow through the capillary of this viscometer. Dynamic mechanical analysis of 22 wt. % aqueous polymer solutions show that the real part ($\eta'$) of complex viscosity increases from 5 to 500 dyne sec cm$^{-2}$ [P] and elastic modulus (G') increased from zero to 100 dyne cm$^{-2}$ during a sol-to-gel transition (FIG. 6). $\eta'$ and G' are measures of dissipated energy and stored energy respectively when a material is subject to cyclic deformation. And, practically no flow was observed above 30° C. in the test-tube inverting method, indicating a sol-to-gel transition. When we compare the two methods for 22 wt % aqueous polymer solutions, the gelation temperature determined by test-tube inverting method corresponds to the temperature at which $\eta'$ of 100 P and G' of 50 dyne/cm$^2$ are reached in dynamic mechanical analysis when thermal equilibrium is assumed in both cases.

The phase diagram of PEG-g-PLGA aqueous solutions determined by a test-tube inverting method is shown in FIG. 6. The sol-to-gel transition is accompanied by a sharp increase in viscosity. The critical gel concentration (CGC) above which the gel phase appears was about 16 wt. %. Below CGC, the system flows even though the viscosity increases as the temperature increases. The sol-to-gel transition temperature, estimated at about 30° C., was slightly affected by the polymer solution concentration. The presence of the gel phase around body temperature (37° C.) indicates that the material is a promising candidate for an injectable drug delivery system that can be formulated at room temperature, and would form a gel in situ upon subcutaneous or intramuscular injection. The pharmaceutical agents would then be slowly released from the in situ formed gel.

Figure 7:
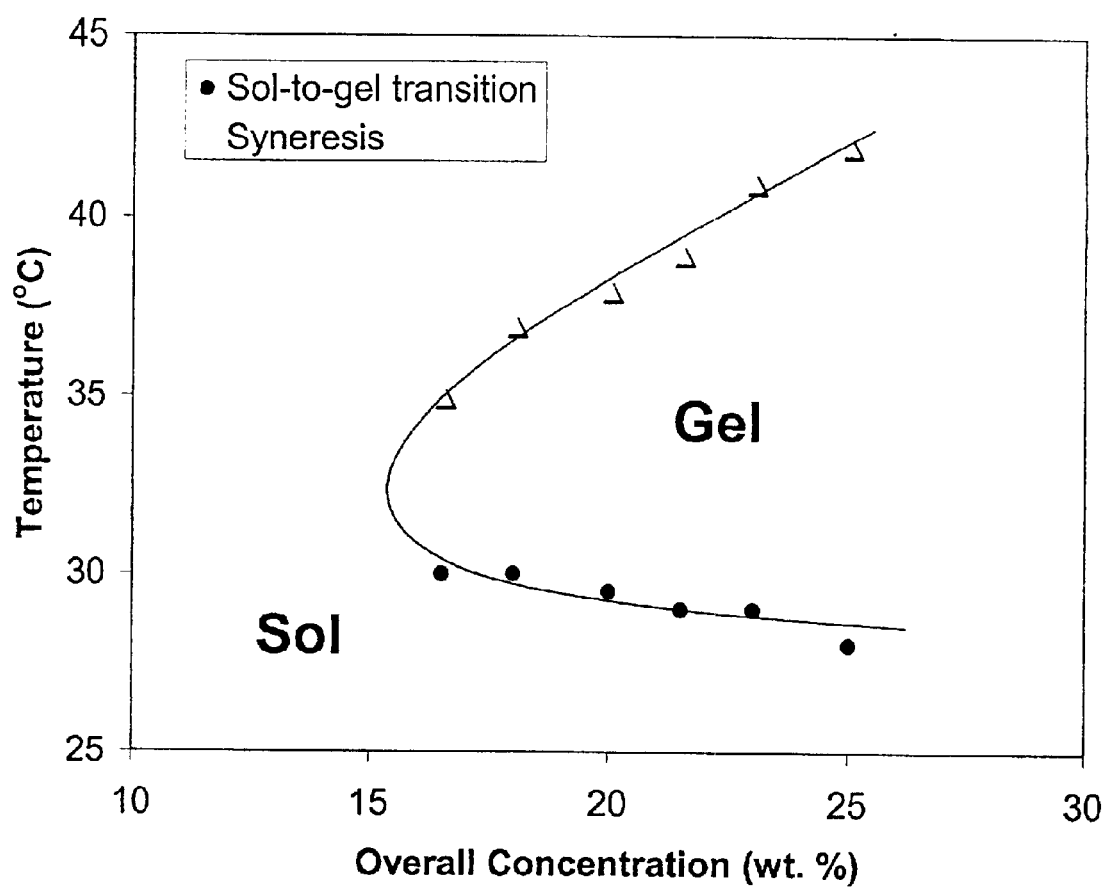
FIG. 7 is a graphical representation of a phase diagram of PEG-g-PLGA aqueous solution.

Further analysis of the phase diagram illustrates that with increasing temperature the gel exhibits syneresis, marked as gray triangles in FIG. 7, a macromolecular phase separation where some amount of water is exuded from the gel phase. Above the syneresis temperature, the gel phase remains separated from the water. Therefore, the sol phase at low temperature is a homogeneous one-phase solution while the sol phase above syneresis is a two-phase system. The gel region, right side of the trend line in the phase diagram indicates the area where a uniform gel phase exists. Based on the phase diagram (FIG. 7), 21–25 wt. % of PEG-g-PLGA aqueous solutions are recommended as injectable formulations for drug delivery.

The aggregation number of a micelle can be estimated from the size of the micelle by assuming that the micelle is a hard sphere. The radius of a micelle can be estimated from equation.

$$R=(3M_{s,D}v_2/4\pi N_A)^{1/3} \qquad \text{a.}$$

Where $M_{s,D}$ denotes the molecular weight of a micelle obtained from centrifugal sedimentation, which is close to weight average molecular weight ($M_w$). $v_2$, and $N_A$ are the partial specific volume of the polymer, and the Avogadro's number, respectively. The aggregation number of a micelle ($N_{ag}$) is given by equation.

$$N_{ag}=M/M_0 \qquad \text{b.}$$

Where M and Mo denote molecular weight of a micelle and molecular weight of a polymer respectively. Assuming $v_2$ is 0.95, which is typical for polyester or polyether, and R is about 4.5 nm (diameter ~9 nm) from Cryo-TEM, the micellar aggregation number is 40 at 20° C. The aggregation number of a micelle is assumed to be practically constant for a sol region as in the cases of PEG-PLGA-PEG and poloxamer 407. This calculation also assumes that M is equal to $M_{s,D}$ and the molecular weight of PEG-g-PLGA ($M_0$) is 6000 as determined from GPC data. Based on this estimation, the thermodynamic functions such as enthalpy ($\Delta H^0$), Gibbs free energy ($\Delta G^0$), and entropy of gelation ($\Delta S^0$) can be calculated. Now, the standard states of gelation process are taken to be the micelles in ideal dilute solution at unit molarity and micelles in gel state.

$$\Delta G^0=RT_{gel}\ln C_m \qquad \text{c.}$$

$$\Delta H^0=R[d \ln C_m/d(1/T_{gel})] \qquad \text{d.}$$

$$\Delta S^0=(\Delta G^0-\Delta H^0)/T_{gel} \qquad \text{e.}$$

Figure 8:
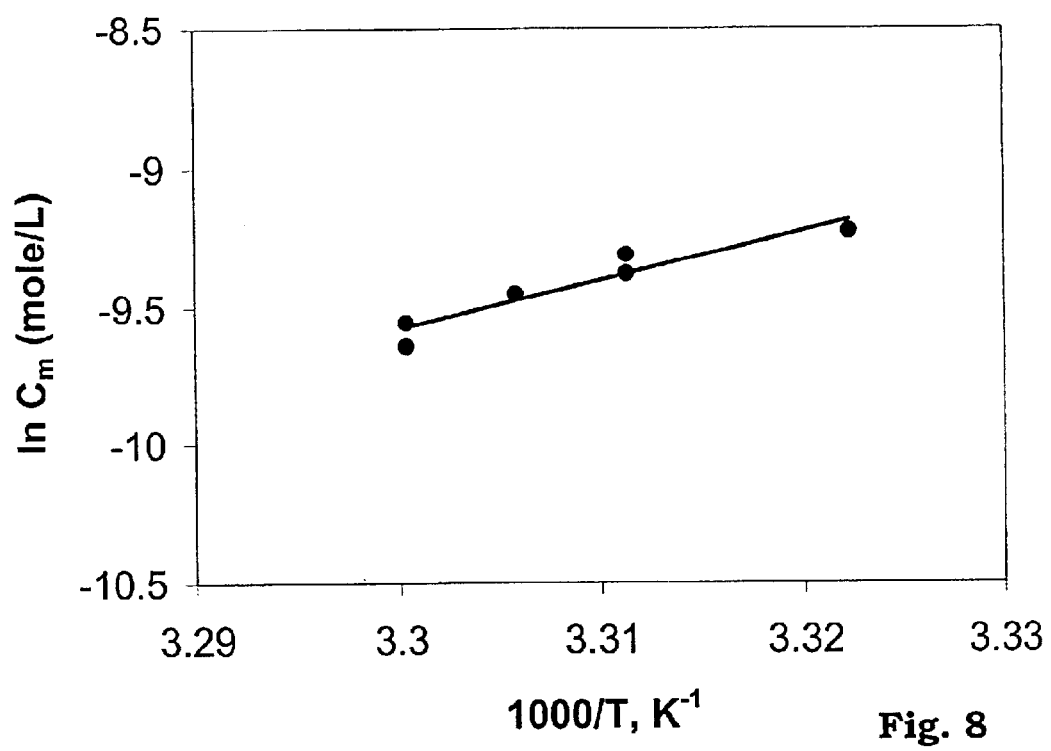
FIG. 8 is a graphical representation of the calculation of enthalpy of sol-to-gel transition of PEG-g-PLGA aqueous solutions.

$C_m$ is the concentration of micelles in mole L$^{-1}$ that is calculated by assuming that the aggregation number per micelle is 40. $T_{gel}$ is the sol-to-gel transition temperature. $\Delta H^0$ calculated from the slope of $\ln C_m$ versus $1/T_{gel}$ (FIG. 8) is 146 kJ mole$^{-1}$ (micelle) or $\Delta H^0$=3.65 kJ mole$^{-1}$ (chain). This value is similar to gelation of poloxamer 407 ($\Delta H^0$=1.5 kJmole$^{-1}$ (chain)) and PEG-PLGA-PEG triblock copolymers ($\Delta H^0$=1.32 kJ mole$^{-1}$ (chain)). Gibbs free energy ($\Delta G^0$) and entropy ($\Delta S^0$) for the gelation of 22 wt. % PEG-g-PLGA aqueous solution with a $T_{gel}$ of 30° C. are −0.59 kJ mole$^{-1}$ and 1.9 J mole$^{-1}$ K$^{-1}$, respectively. This calculation leads to the conclusion that the entropy drives the gelation. The molecular origin of such an entropy-driven process has been suggested as hydrophobic interactions. Water molecules tend to surround the hydrophobic segment (PLGA) to decrease the free energy. Consequently, the entropy of water molecules decreases in the presence of hydrophobes. Therefore, the surface area of hydrophobic molecules is minimized in water. Such hydrophobic interactions increase with increasing temperature, and change the molecular conformation of PEG-g-PLGA, thus might drive the gelation.

Figure 9:
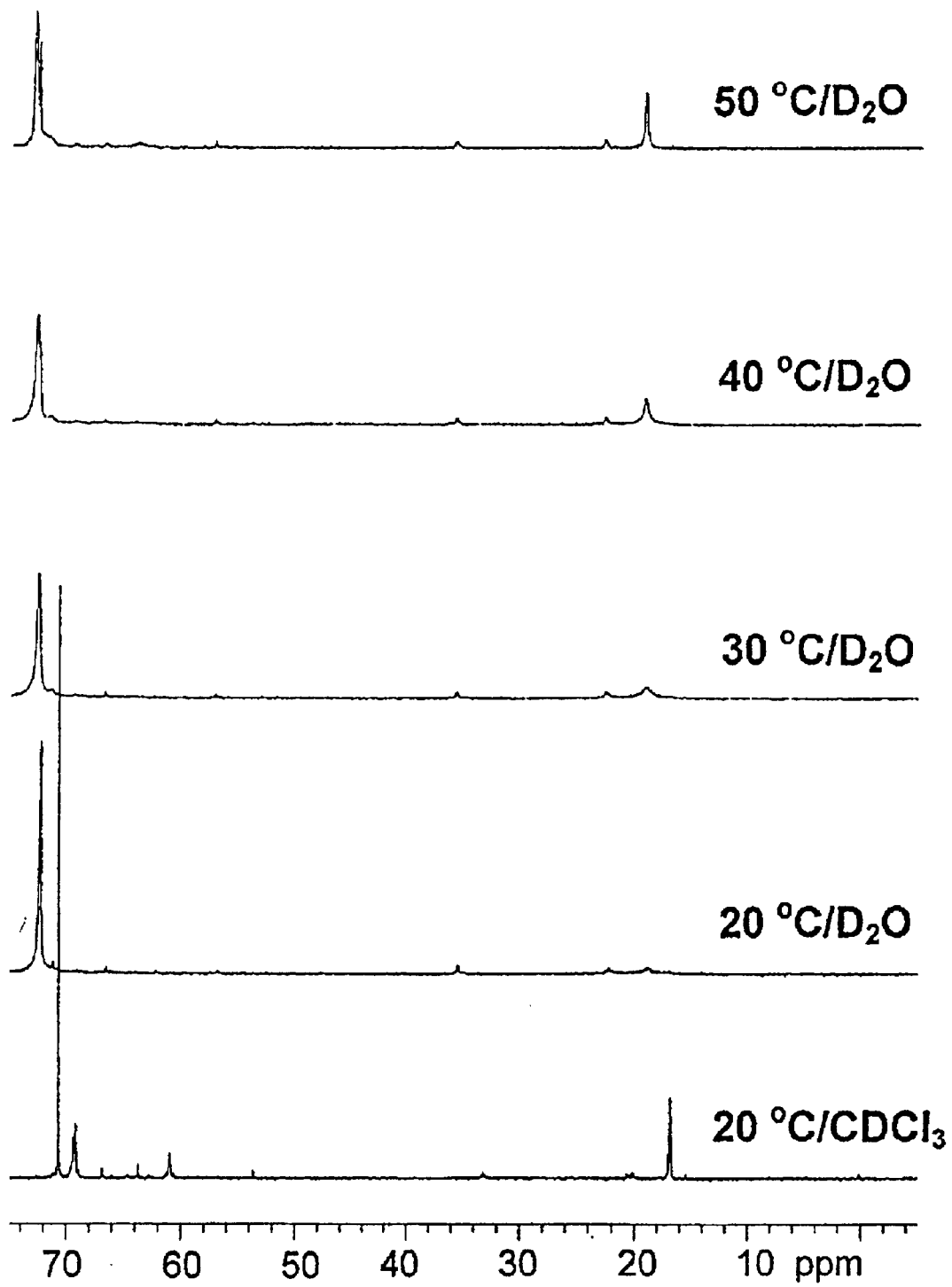
FIG. 9 is a graphical representation of the $^{13}$C-NMR spectra of PEG-g-PLGA in $D_2O$ (22 wt. %) as a function of temperature.

The $^{13}$C-NMR analysis of the polymers was conducted at different temperatures to elucidate the structure of the gel and mechanism of gel formation (FIG. 9). Spectra of polymers dissolved in water and chloroform were compared. The $^{13}$C-NMR spectra of a 22 wt. % PEG-g-PLGA in D$_2$O were obtained at 20 (sol state), 30 (just above sol-to-gel transition), 40 (gel state), and 50° C. (macrophase-separated state) by simply increasing the temperature around the probe without changing NMR parameters. The equilibration time at each temperature was 15 minutes. Chloroform (CDCl$_3$) is a nonselective good solvent for both PEG and PLGA blocks while water (D$_2$O) is a good solvent for PEG but is a poor solvent for PLGA. The sharp peaks of both PEG and PLGA in chloroform are compared with a collapsed peak of PLGA in water at first and second rows of $^{13}$C-NMR, indicating core (PLGA)-shell (PEG) structure of the polymer in water. The molecular motion of PEG in water is decreased due to anchoring effects by the hydrophobic PLGA segments compared with that in chloroform. This fact is reflected in a broadened peak of PEG in D$_2$O at 20° C. The change in molecular association at sol-to-gel transition involves the change in molecular motion of the polymers. The change in $^{13}$C-NMR with increasing temperature (20° C.–50° C.) shows such a change in microenvironment around the PEG and PLGA. The PEG peak (72 ppm) at a gel state (30° C.) is broadened and decreased by half in height compared with a sol state (20° C.), whereas there is a slight increase in PLGA peak height (20 ppm) at gel state (30° C.). These changes in peak heights indicate a significant decrease in molecular motion of the PEG backbone, and increased thermal motions of the PLGA side chains during sol-to-gel transition. This behavior is quite different from that of PLGA-g-PEG. PLGA-g-PEG showed little change in PEG peak during sol-to-gel transition at the $^{13}$C-NMR in D$_2$O. Based on these observations, the following model can be suggested for the sol-to-gel transition of PEG-g-PLGA copolymer aqueous solutions. In a sol state, the polymer conformation is micellar where the PEGs occupy shell and PLGAs occupy core of the micelle. The degree of association in a sol state is not enough to form a three dimensional network. With increasing temperature, the hydrophobic interactions increase and associations of polymers decrease the PEG molecular motion, resulting in a long-range network formation, that is, a gel. The degree of association is strong enough to keep its integrity in the presence of excess water at a given temperature such as 37° C. Therefore, we can define this system as a gel rather than a solution with an increased viscosity. As the temperature increases further, the long-range interactions among the polymers increase and phase mixing between PEG and PLGA occurs, resulting in the macrophase separation between water and polymer that occurs at 50° C.

The 22 wt. % polymer solutions (0.5 g) are injected into 4 mL vials (diameter of 1.1 cm) and kept in a 37° C. water bath for five minutes. During this time the gel forms. 3 mL of phosphate buffer saline (37° C., pH=7.4) is added and the vials are shaken (16 strokes/minute) in the water bath to simulate body condition. The gel keeps its integrity for one-week in vitro, and the initially turbid gel becomes transparent in 3 to 7 days. After 7 days, the gel totally disintegrated to become a clear polymer solution.

This material can be applied for a short-term delivery of bioactive agents such as pharmaceutical drugs (e.g. proteins, anticancer drugs) as well as a carrier or delivery system for bioactive agents used in tissue engineering. The hydrophobicity of the drug and the molecular structure of the polymers affect the extent of diffusion or degradation dominant drug release profile. Therefore, by choosing the appropriate drug and molecular parameters of PEG-g-PLGA, a short-term delivery system can be designed based on this polymer hydrogel.

Synthesis: One-Step Synthesis of PLGA-g-PEG

The graft copolymer PLGA-g-.PEG was synthesized by a one-step ring opening polymerization of DL-lactide, glycolide, and epoxy terminated poly(ethylene glycol) (PEG; m.w.=600) using stannous octoate as a catalyst. The DL-lactic acid/glycolic acid/ethylene glycol mole ratio is 3.2/1/2.8, which was determined by H-NMR. Therefore, the grafting frequency of PEG is 4.7% by mole. Therefore, the grafting frequency of PEG is 4.7 % by mole. Gel permeation chromatography (GPC) using light scattering and refractive index detectors in series can give absolute molecular weight of polymers. (P. J. Wyatt. Anal. Chim. Acta, 1993, 272, 1) GPC shows a unimodal curve. The number average molecular weight (Mn) and polydispersity (Mw/Mn) of the polymers determined by GPC using tetrahydrofuran (THF) as an eluting solvent are 9300 and 1.5, respectively. Therefore, the 4~5 PEGs are grafted on a PLGA backbone.

Sol-Gel Transition:

At room temperature, viscosity of the 25 wt. % aqueous solutions is about 0.3 poise (gm$^{-1}$s$^{-1}$), which allows for injecting the solution using a 25-gauge needle. With increasing temperature, the aqueous solutions (25 wt. %) of PLGA-g-PEG undergo a sol-to-gel transition at 30° C. The gel state is traditionally defined as a non-flowing semisolid by a test-tube inversion method. In the practical application, the gel should keep its equilibrium-swollen state and not dissolve in an excess amount of solvent. Further increase in temperature of the PLGA-g-PEG aqueous solution (25 wt. %) results in a macroscopic phase-separation between gel and water, that is, syneresis occurs at 50° C.

Dynamic Mechanical Analysis:

The sol-gel transition of the graft copolymer aqueous solution was investigated using dynamic rheometry (Rheometric Scientific: SR 2000) in a similar manner to poloxamer aqueous solutions. The polymer solution was placed between parallel plates having a diameter of 25 mm and a gap distance of 0.5 mm. The data were collected under controlled stress (4.0 dyne/cm$^2$) and a frequency of 1.0 radian/second. The heating and cooling rate was 0.2° C./min. By the dynamic mechanical analysis, sol-gel transition can be identified in a more reproducible and quantitative manner than the test-tube inversion method.

Figure 10:
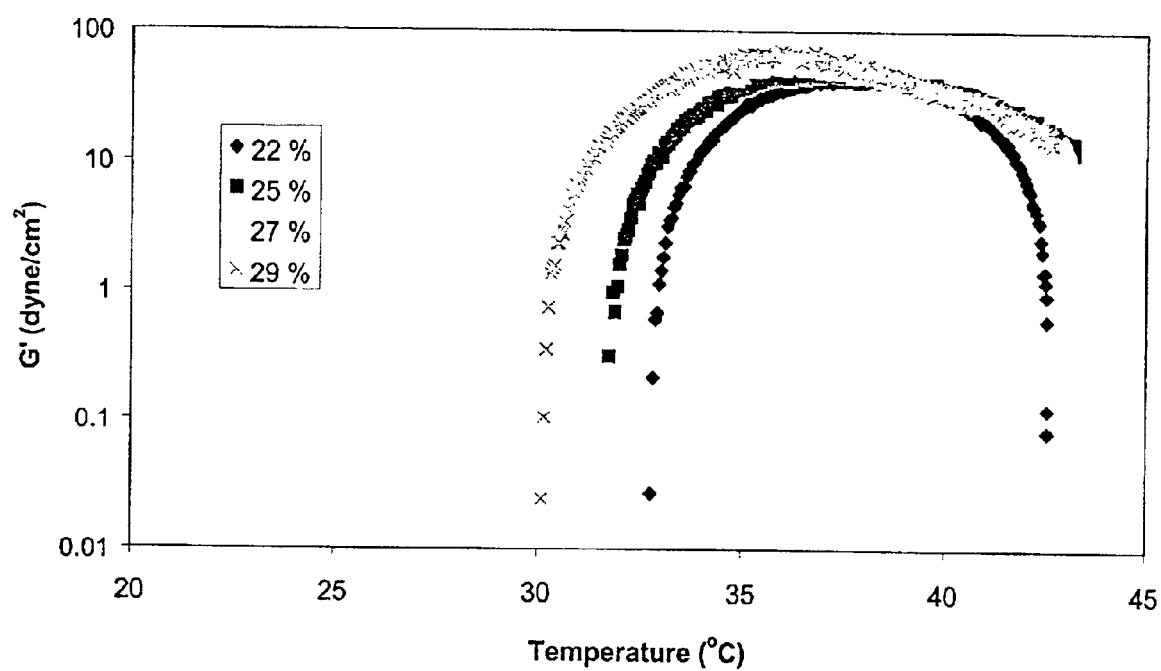
FIG. 10 is a graphical representation of the storage modulus of PLGA-g-PEG as a function of temperature and concentration.

The modulus of the PLGA-g-PEG aqueous solution is shown in FIG. 10 as a function of temperature and concentration. The storage modulus increases abruptly at the sol-to gel transition. The gels have a modulus of about 50 dyne/cm$^2$ and are slightly affected by concentration in a range of 22 to 29 wt. %. The sol-to-gel transitions occur at around 30° C., suggesting easy formulation at room temperature.

Figure 11A:
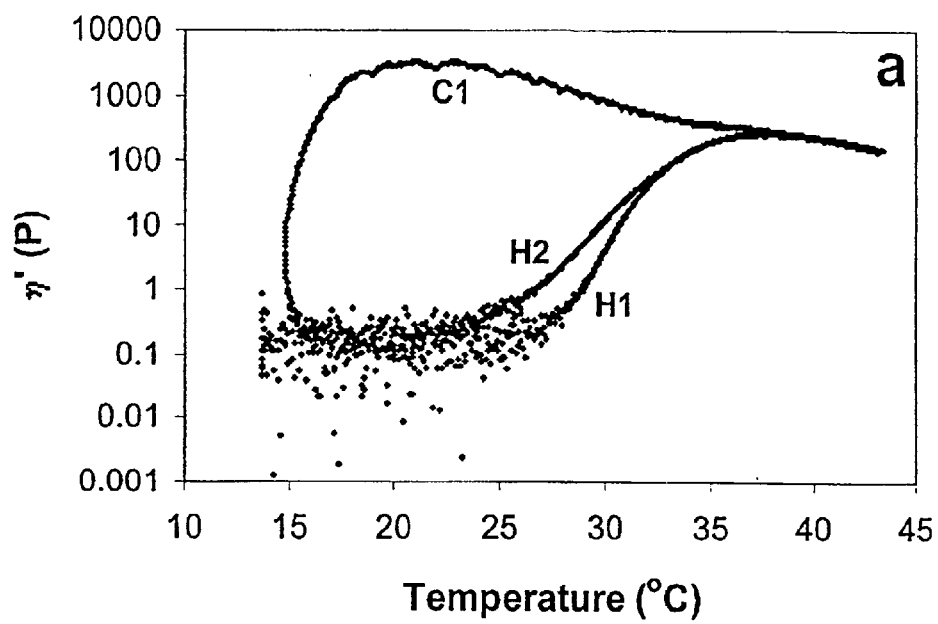
FIG. 11a is a graphical representation of a Theological study of PLGA-g-PEG copolymer aqueous solutions (25 wt. %) wherein the real part (η') of complex viscosity of the copolymer solution was measured as a function of temperature.

To confirm the reversibility of the sol-gel transition, 25 wt. % PLGA-g-PEG aqueous solutions were studied. The real part (η') of complex viscosity of the polymer solution, which is a measure of dissipated energy when cyclic deformation is applied to a material, is shown as a function of temperature in FIG. 11a. During the first heating cycle (H1), η' increased 1000 times upon sol-to-gel transition. The cooling curve (C1) shows that the gel phase persisted over the temperature range of 43~20° C. in the experimental time scale. This fact results from the difficulty in molecular rearrangement in the gel phase; once the solution forms a gel, the molecules resist disintegration. η' abruptly decreased at 15° C. due to gel-to-sol transition during the cooling of the system. The second heating curve (H2) shows sol-to-gel transition at practically the same temperature as the first heating curve (H1).

Figure 11B:
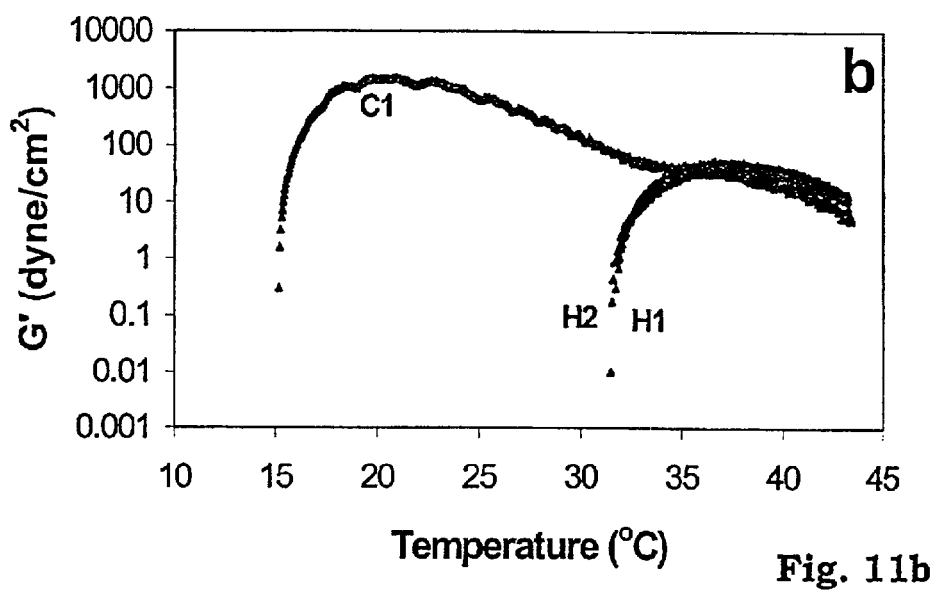
FIG. 11b is a graphical representation of a Theological study of PLGA-g-PEG copolymer aqueous solutions (25 wt. %) wherein the storage modulus (G') of the copolymer solution was measured as a function of temperature.
Figure 12:
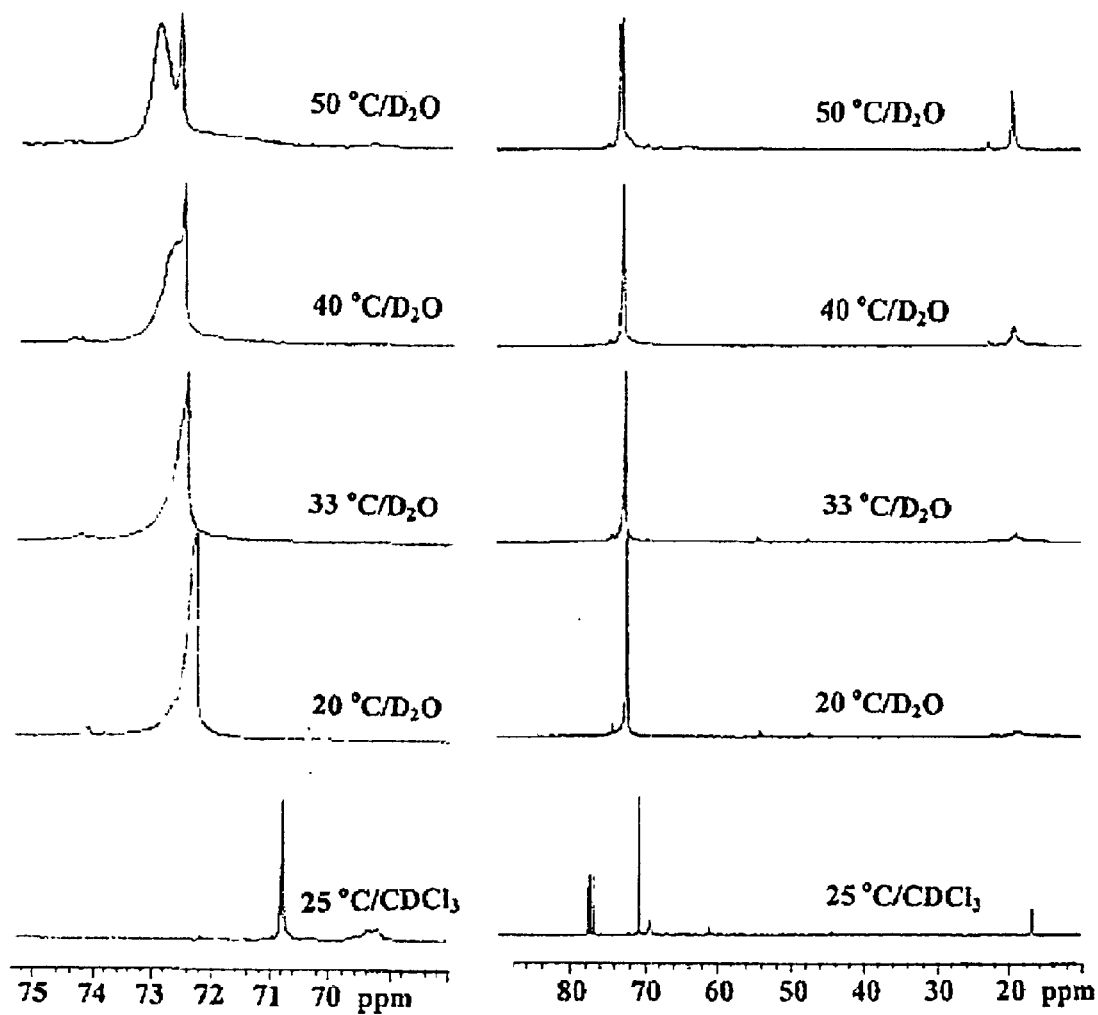
FIG. 12 is a graphical representation of a $^{13}$C-NMR (75 MHz) spectra of 25% (wt.) PLGA-g-PEG copolymer in $D_2O$ as a function of temperature wherein the zoom spectra (~73 ppm) are shown at left.

The storage moduli (G') of the PLGA-g-PEG aqueous solutions (25 wt. %), which are a measure of stored energy when a cyclic deformation is applied to a material, are practically zero at a sol state and are not shown in the heating curve (FIG. 11b; H1). G'sharply increased during sol-to-gel transition at 32° C. as shown in heating curves. The maximum value for G' was measured between 35~39° C., indicating a promising material for in-vivo (37° C.) applications. During the cooling cycle (C1), the gel modulus increased over the temperature range of 43~20° C., exhibiting similar behavior to typical elastic materials, and dropped abruptly at 15° C. due to gel-to-sol transition. During the first (H1) and second (H2) heating cycle, practically the same transition curve was measured for G', indicating a reversible gelation. The decrease in G' at temperatures above 40~45° C. can be expected due to increase in thermal motion. This trend was also observed with $^{13}$C-NMR spectra (FIG. 12).

NMR Study:

The $^{13}$C-NMR spectra of a 25 wt. % copolymer solution in D$_2$O were recorded at different temperatures. In the sol state (20° C.), the methyl peak of the hydrophobic PLGA (18 ppm) is collapsed and broadened compared with PEG peak (72 ppm) whereas that in CDCl$_3$ appears as a sharp peak, indicating core-shell structure of this polymer in water. The core-shell structure of these amphiphilic copolymers was also confirmed by micelle formation in diluted aqueous solutions. The critical micelle concentration (CMC) determined by a dye solubilzation method was 0.03 wt. % at 20° C.

Just above the sol-to-gel transition temperature (33° C.) of an aqueous PLGA-g-PEG copolymer solution (25 wt. %), the $^{13}$C-NMR peak shapes of both the hydrophobic PLGA methyl peak and hydrophilic PEG peak are preserved except that the PEG peak was shifted down field about 0.3 ppm. With a further increase in temperature, the peak height of the PLGA methyl peak increases, and the PEG peak is split into two peaks, a sharp one at 72.4 ppm and a broad one at 72.7 ppm. These behaviors are thought to be caused by an increase in molecular motion of the hydrophobic backbone and phase mixing between PEG and PLGA. The phase mixing between PEG and PLGA or PLLA was previously reported. Further increase in temperature resulted in macrophase separation between water and the polymer.

Figure 13:
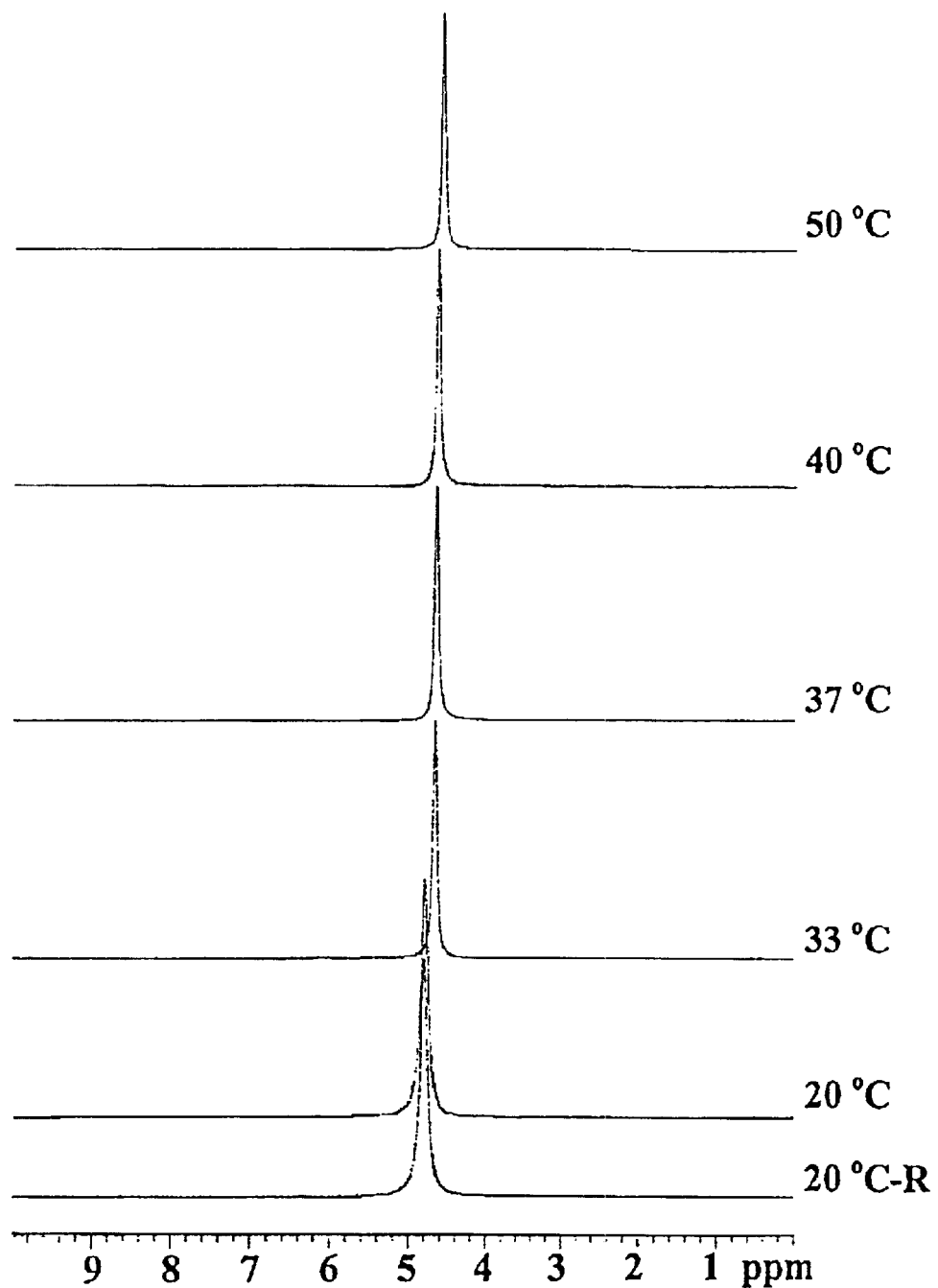
FIG. 13 is a graphical representation of a deuterium NMR showing reversibility of the sol-gel transition.

The reversibility of the sol-gel transition is also confirmed by deuterium NMR (FIG. 13). The peak at 4.8 ppm at 20° C. (sol state) shifted to 4.6 ppm at 33° C. (just above sol-to-gel transition), 4.58 ppm at 37° C. (gel state), 4.56 ppm at 40° C., and 4.5 ppm at 50° C. (syneresis). The change in chemical shift was the most pronounced during the sol-to-gel transition ($\delta$=0.2 ppm) and then during syneresis. When the system is cooled to 20° C., the deuterium peak reappears at 4.8 ppm, indicating the reversibility of the transition. In a sol state, water moves more freely than in a gel state. During the sol-to-gel transition, PEG becomes more hydrophobic due to dehydration and the extent of hydrogen bonding between water molecules and polymers changes. Therefore, the time average environment around deuterium nuclei will be affected, leading to the changes in chemical shift of water during sol-to-gel transition. This finding suggests that the deuterium NMR can be a good method for the determination of sol-gel transition.

The sol-to-gel transition temperature could be controlled from 20° to 40° C. by changing PEG length and composition. When the PEG molecular weight of PLGA-g-PEG increases from 600 to 1000 the sol-to-gel transition occurred at 40° C., whereas the sol-to-gel transition occurred at 20° C. when the PEG composition is decreased by 20% in mole.

Varying Gel Durability:

The time frame for gel durability can be varied by adjusting the ratio of the two blocks in the formula $A_n(B)$ (where n is >2). To test and exemplify the duration of a gel 0.5 g of a polymer solution (see table below) was injected into a 4 ml vial (inner diameter 1.1 cm) and maintaining at 37° C. for 5 minutes to allow the gel to form. After the gel is formed, 3 ml of phosphate buffer saline (37° C., pH=7.4) is added and the vial is placed in a shaker bath (16 strokes/minute). The polymer was monitored daily for complete degradation and the top layer of the buffer was replaced at the time of monitoring. The following table shows the resulting gel durations for each ration of the polymer. PEG-g-PLGA had a molecular weight of 11,000 and PLGA-g-PEG had a molecule weight of 7,800.

| Ratio (PEG-g-PLGA/PLGA-g-PEG) | 100/0 | 60/40 | 50/50 | 40/60 | 0/100 |
|---|---|---|---|---|---|
| Duration of a gel measured as described above. | 1 day~1 week | 3 days~ 2 weeks | 2~ 4 weeks | 3~6 weeks | 6~ 10 weeks |

Conclusions

The aqueous solutions of PEG-g-PLGA copolymers exhibited sol-to-gel transition in response to an increase in temperature. Micelle formation was confirmed by Cryo-TEM and dye solubilization method. The micellar diameter was about 9 nm and CMC was in a range of 0.01–0.05 wt. %. $^{13}$C-NMR shows that the molecular motion of PEG backbones decreases while that of PLGA side chains increases during sol-to-gel transition.

The 21–25 wt. % solutions exhibit low viscosity at room temperature and form gels at body temperature. The gel morphology changed from turbid to transparent, and the integrity of gel persisted for one week suggesting a promising candidate for short-term drug delivery systems.

The aqueous PLGA-g-PEG system showing a reversible sol-to-gel transition by increasing temperature was studied by dynamic mechanical analysis and NMR spectrophotometer. The rheological study of the copolymers in aqueous solution demonstrated that thermogelation occurred at about 30° C. and the elastic gel modulus exhibited a maximum around body temperature (37° C.). A preliminary in vivo study in a rat model confirmed in situ gel formation after subcutaneous injection of a 0.5 ml aqueous solution. The gel was still present at the injection site after 2 months. This fact clearly distinguishes this polymer from poly(ethylene glycol)-g-poly(DL-lactic acid-co-glycolic acid) PEG-g-PLGA copolymer hydrogels, which disintegrated in one week.

The system developed in this study is very promising for local delivery of bioactive agents such as proteins, anticancer drugs, and antiathritis drugs by subcutaneous, intraperitoneal, ocular, vaginal or rectal administrations. Thermosensitivity enables the in-situ gel formation upon injection, therefore no surgical procedure is required to implant the drug delivery system and no organic solvent is needed for drug formulation. The physical properties of soft hydrogels reduce mechanical tissue irritation surrounding the injection site. Also, the polymers are biodegradable; therefore there is no need for surgical removal of the implant after the release of the pharmaceutical agent.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claim.

We claim:

1. A thermogelling biodegradable aqueous polymer solution, comprising:
   a. a biodegradable graft polymer, comprising:
      i. a polyethylene glycol (PEG) block, and
      ii. a biodegradable polyester block, wherein
      iii. said blocks are linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B; and
   b. an aqueous solution.

2. A thermogelling biodegradable aqueous polymer solution according to claim 1 wherein n is between 3 and 10.

3. A thermogelling biodegradable aqueous polymer solution according to claim 1 wherein said polyethylene glycol (PEG) has a weight average molecular weight of between about 300 and 20,000.

4. A thermogelling biodegradable aqueous polymer solution according to claim 1 wherein said polyethylene glycol (PEG) has a weight average molecular weight of between about 500 and 10,000.

5. A thermogelling biodegradable aqueous polymer solution according to claim 1 wherein said polyester block has a weight average molecular weight of between about 1,000 and 30,000.

6. A thermogelling biodegradable aqueous polymer solution according to claim 1 wherein said polyester block has a weight average molecular weight of between about 1,000 and 10,000.

7. A thermogelling biodegradable aqueous polymer solution according to claim 1, wherein said biodegradable polyester block is selected from the group consisting of poly (DL-lactic acid), poly(L-lactic acid), poly(glycolic acid), poly($\epsilon$-caprolactone), poly($\gamma$-butyrolactone), poly($\gamma$-valerolactone), poly($\beta$-hydroxybutyric acid), and their copolymers or terpolymers.

8. A thermogelling biodegradable aqueous polymer solution according to claim 7, wherein said copolymers and/or terpolymers are selected from the group consisting of poly (DL-lactic acid-co-glycolic acid), poly(L-lactic acid-co-glycolic acid), poly($\epsilon$-caprolactone-co-DL-lactic acid), copoly($\epsilon$-caprolactone-co-DL-lactic acid-glycolic acid).

9. A biodegradable bioactive agent delivery system, comprising:
   a. an effective amount of bioactive agent contained in;
   b. a thermogelling biodegradable aqueous polymer solution comprising
      i. a biodegradable graft polymer, comprising a polyethylene glycol (PEG) block, a biodegradable polyester block, wherein said blocks are linked to form a polymer of a general structure comprising the formula $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B, and
      ii. an aqueous solution.

10. A biodegradable bioactive agent delivery system according to claim 9 wherein said bioactive agent is a drug.

11. A biodegradable bioactive agent delivery system according to claim 10 wherein said drug is selected from the group consisting of anti-cancer agents, hormones, antibiotics, narcotic antagonists, analgesics, anti-inflammatory agents, anti-depressants, anti-epileptics, anti-malarial agents, immunoactivators, growth factors, radio-protection agents, vaccines, gene therapy agents, oligonucleotides, antisense, peptides and proteins, and combinations thereof.

12. A biodegradable bioactive agent delivery system according to claim 10 wherein said drug is an anti-cancer agent.

13. A biodegradable bioactive agent delivery system according to claim 12 wherein said anti-cancer agent is a member selected from the group consisting of adriamycin, mitomycin, bleomycin, cisplatin, carboplatin, doxorubicin, daunorubicin, 5-fluouroacil, methotrexate, taxol, taxotere, and actinomycin D.

14. A biodegradable bioactive agent delivery system according to claim 10 wherein said drug is a polypeptide.

15. A biodegradable bioactive agent delivery system according to claim 14 wherein said polypeptide is a member selected from the group consisting of oxytocin, vasopressin, adrenocorticotropic growth factor (PDGF), prolactin, luliberin or luteinising hormone releasing hormone (LHRH), growth hormone, growth hormone releasing factor, insulin, somatostatin, glucagons, interleukin-2 (IL-2), interferon-$\alpha$, $\beta$,$\gamma$ (IFN-$\alpha$,$\beta$,$\gamma$), gastrin, tetragastrin, pentagastrin, urogastroine, secretin, cacitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (M-CSF), rennin, bradykinin, bacitracins, alpha-1 antitrypsin, platelet derived growth factor, albumin, anti-thrombin III, glucocerebrosidase, DNAse, tissue plasminogen activator, calcitonin, clotting factors VII, VIII, and IX, LHRH antagonists, insulin, erythropoietin, polymixins, colistins, tyrocidin, gramicidines, and synthetic analogues, modifications and pharmacologically active fragments thereof, monoclonal antibodies and soluble vaccines.

16. A biodegradable bioactive agent delivery system according to claim 9 wherein said therapeutic agent is a cell.

17. A biodegradable bioactive agent delivery system according to claim 9 wherein said thermogelling biodegradable aqueous polymer solution provides as a solubilizer.

\* \* \* \* \*

UNITED STATES PATENT AND TRADEMARK OFFICE
CERTIFICATE OF CORRECTION

PATENT NO. : 6,841,617 B2
APPLICATION NO. : 09/833460
DATED : January 11, 2005
INVENTOR(S) : Byeongmoon Jeong and Anna Gutowska It is certified that error appears in the above-identified patent and that said Letters Patent is hereby corrected as shown below:

On the Cover page, item [56]

Under OTHER PUBLICATIONS, in the Brown, W. et al., reference, "Poly-(ethylene oxide) Poly(propylene oxide) Poly(ethylene oxide)" should read -- Poly-(ethylene oxide)/Poly(propylene oxide)/Poly(ethylene oxide) --

Under OTHER PUBLICATIONS, in the Cau, F. et al., reference, " "HNMR" should read -- $^1$H NMR --

Under OTHER PUBLICATIONS, in the Chen, G. et al., reference, "p11" should read -- pH --

Under OTHER PUBLICATIONS, the following references should be included:
Discher, BM. Et al., *"Polymersomes: Tough Vesicles Made From Diblock Copolymers."* Pg. 1-9, 1999.
Feil, H. et al., *"Effects of Comonomer Hydrophilicity and Ionization on the Lower Critical Solution Temperature of N-Isopropylacrylamide Copolymers."* Pg. 2496-2500. 1993.
Gutowska, A. et al., *"Injectable Gels for Tissue Engineering."* Pg. 1-26. 2000.

On Page 2 of the cover, under OTHER PUBLICATIONS, in the second reference, "Getting" should read -- Gelling --

On Page 2 of the cover, under OTHER PUBLICATIONS, in the Wout, ZGM. et al., reference, "40$^7$" should read -- 407 --

On Page 2 of the cover, under OTHER PUBLICATIONS, in the Yu, GE. et al., reference, "Miceiisation" should read -- Micellisation --

On Page 2 of the cover, under OTHER PUBLICATIONS, in the Moiseev, L., reference, "http: www.bu.edu mebb calendar of events abstracts moiseev abstract.htm" should read
-- http:www.bu.edu/mcbb/calendar_of_events/abstracts/moiseev_abstract.htm --

UNITED STATES PATENT AND TRADEMARK OFFICE
CERTIFICATE OF CORRECTION

PATENT NO. : 6,841,617 B2
APPLICATION NO. : 09/833460
DATED : January 11, 2005
INVENTOR(S) : Byeongmoon Jeong and Anna Gutowska It is certified that error appears in the above-identified patent and that said Letters Patent is hereby corrected as shown below:

In Column 2, line 48, "wwvv" should read -- www. --

In Column 5, line 24, "Theological" should read -- Rheological --

In Column 5, line 29, "Theological" should read -- Rheological --

Signed and Sealed this

Eighth Day of August, 2006

JON W. DUDAS
*Director of the United States Patent and Trademark Office*